(12) United States Patent
Garten et al.

(10) Patent No.: US 10,770,604 B2
(45) Date of Patent: Sep. 8, 2020

(54) HYBRID PEROVSKITE BULK PHOTOVOLTAIC EFFECT DEVICES AND METHODS OF MAKING THE SAME

(71) Applicants: Alliance for Sustainable Energy, LLC, Golden, CO (US); Colorado School of Mines, Golden, CO (US)

(72) Inventors: Lauren Marie Garten, Lakewood, CO (US); David Todd Moore, Lakewood, CO (US); David Samuel Ginley, Evergreen, CO (US); Brian Patrick Gorman, Golden, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 104 days.

(21) Appl. No.: 15/934,656

(22) Filed: Mar. 23, 2018

(65) Prior Publication Data
US 2018/0277695 A1     Sep. 27, 2018

Related U.S. Application Data

(60) Provisional application No. 62/476,492, filed on Mar. 24, 2017.

(51) Int. Cl.
*H01L 31/032*     (2006.01)
*C07C 211/04*     (2006.01)
(Continued)

(52) U.S. Cl.
CPC .......... *H01L 31/032* (2013.01); *C07C 211/04* (2013.01); *H01L 31/068* (2013.01);
(Continued)

(58) Field of Classification Search
CPC ... H01L 31/032; H01L 31/04; H01L 51/4206; H01L 51/4213
(Continued)

(56) References Cited

U.S. PATENT DOCUMENTS 2,852,400 A    9/1958  Remeika
5,248,564 A    9/1993  Ramesh
(Continued)

OTHER PUBLICATIONS

Garten et al, The field induced e31,f piezoelectric and Rayleigh response in barium strontium titanate thin films, Aug. 2014, Applied Physics Letters 105, 132905, 1-4. (Year: 2014).*
(Continued)

*Primary Examiner* — Andrew J Golden
(74) *Attorney, Agent, or Firm* — Michael A. McIntyre

(57) ABSTRACT

The present disclosure relates to a composition that includes a perovskite crystal having a ferroelectric domain aligned substantially parallel to a reference axis. In some embodiments of the present disclosure, the perovskite crystal may include $ABX_3$, where A is a first cation, B is a second cation, and X is an anion. In some embodiments of the present disclosure, A may include an alkyl ammonium cation. In some embodiments of the present disclosure, B may include a metal element. In some embodiments of the present disclosure, the metal element may include lead. In some embodiments of the present disclosure, X may include a halogen. In some embodiments of the present disclosure, the perovskite crystal may include methylammonium lead iodide.

7 Claims, 25 Drawing Sheets

(51) Int. Cl.
   *H01L 31/068* (2012.01)
   *H01L 51/42* (2006.01)
   *H01L 41/193* (2006.01)
(52) U.S. Cl.
   CPC ........ *H01L 51/4206* (2013.01); *H01L 41/193* (2013.01); *H01L 51/4213* (2013.01)
(58) Field of Classification Search
   USPC .............................................. 136/243–265
   See application file for complete search history.

(56) References Cited

U.S. PATENT DOCUMENTS

| | | | |
|---|---|---|---|
| 5,514,484 A | 5/1996 | Nashimoto | |
| 2010/0289377 A1* | 11/2010 | Erbil | H01L 37/02 310/306 |
| 2012/0017976 A1* | 1/2012 | Nechache | H01L 31/032 136/255 |
| 2020/0119256 A1* | 4/2020 | Chen | H01L 41/193 |

OTHER PUBLICATIONS

Seol et al, Screening effect on photovoltaic performance in ferroelectric CH3NH3PbI3 perovskite thin films, Aug. 2015, J. Mater. Chem. A, 3, 20352-20358. (Year: 2015).*

Liu et al, Photoferroelectric and Photopiezoelectric Properties of Organometal Halide Perovskites, Mar. 2016, J. Phys. Chem. Lett., 7, 1460-1465. (Year: 2016).*

Guo et al, Re-Entrant Relaxor Ferroelectricity of Methylammonium Lead Iodide, United States: N. p., 2016. Web. doi:10.1016/j.cap. 2016.09.016. (Year: 2016).*

Radzi et al, Investigation of Piezoelectric Charge Coefficient d33 of Thick-Film Piezoelectric Ceramics by Varying Poling and Repoling Conditions, May 2015, AIP Conference Proceedings 1660, 070083. (Year: 2015).*

Baikie, T. et al., "A combined single crystal neutron/X-ray diffraction and solid-state nuclear magnetic resonance study of the hybrid perovskites $CH_3NH_3PbX_3$ (X=I, Br and Cl)," Journal of Materials Chemistry A, vol. 3, 2015, pp. 9298-9307.

Beecher A. et al., "Direct Observation of Dynamic Symmetry Breaking above Room Temperature in Methylammonium Lead Iodide Perovskite," ACS Energy Letters, vol. 1, 2016, pp. 880-887.

Butler, K. et al., "Ferroelectric materials for solar energy conversion: photoferroics revisited," Energy & Environmental Science, vol. 8, 2015, pp. 838-848.

Chen, H. et al., "Emergence of Hysteresis and Transient Ferroelectric Response in Organo-Lead Halide Perovskite Solar Cells," Journal of Physical Chemistry Letters, vol. 6, 2015, pp. 164-169.

Choi, W. et al., "Band gap tuning in ferroelectric $Bi_4Ti_3O_{12}$ by alloying with $LaTMO_3$ (TM=Ti, V, Cr, Mn, Co, Ni, and Al)," Applied Physics Letters, vol. 100, 2012, pp. 132903-1 through 132903-3.

Coll, M. et al., "Polarization Switching and Light-Enhanced Piezoelectricity in Lead Halide Perovskites," Journal of Physical Chemistry Letters, vol. 6, 2015, pp. 1408-1413.

Fan, Z. et al., Ferroelectricity of CH3NH3PbI3 Perovskite, Journal of Physical Chemistry Letters, vol. 6, 2015, pp. 1155-1161.

Filippetti, A. et al., "Entropy-Suppressed Ferroelectricity in Hybrid Lead-Iodide Perovskites," Journal of Physical Chemistry Letters, vol. 6, 2015, pp. 4909-4915.

Frost, J. et al., "Atomistic Origins of High-Performance in Hybrid Halide Perovskite Solar Cells," ACS Nano Letters, vol. 14, 2014, pp. 2584-2590.

Frost, J. et al., "Molecular ferroelectric contributions to anomalous hysteresis in hybrid perovskite solar cells," Applied Materials, vol. 2, 2014, pp. 081506-1 through 081506-10.

G, S. et al., "Is $CH_3NH_3PbI_3$ Polar"?, Journal of Physical Chemistry Letters, vol. 7, 2016, pp. 2412-2419.

Grinberg, I. et al., "Perovskite oxides for visible-light-absorbing ferroelectric and photovoltaic materials," Nature, vol. 503, Nov. 2013, 9 pages.

Hoque, Md et al., "Polarization and Dielectric Study of Methylammonium Lead Iodide Thin Film to Reveal its Nonferroelectric Nature under Solar Cell Operating Conditions," ACS Energy Letters, vol. 1, 2016, pp. 142-149.

Hoye, R. et al., "Perovskite-Inspired Photovoltaic Materials: Toward Best Practices in Materials Characterization and Calculations," ACS Chemistry of Materials, vol. 29, 2017, pp. 1964-1988.

Kutes, Y. et al., "Direct Observation of Ferroelectric Domains in Solution-Processed $CH_3NH_3PbI_3$ Perovskite Thin Films," Journal of Physical Chemistry Letters, vol. 5, 2014, pp. 3335-3339.

Kutes, Y. et al., Supporting Information for "Direct Observation of Ferroelectric Domains in Solution-Processed $CH_3NH_3PbI_3$ Perovskite Thin Films," Journal of Physical Chemistry Letters, vol. 5, 2014, 2 pages.

Leguy, A. et al., "The dynamics of methylammonium ions in hybrid organic-inorganic perovskite solar cells," Nature Communications, Jul. 2015, 11 pages.

Leijtens, T. et al., "Stability of Metal Halide Perovskite Solar Cells," Advanced Energy Materials, Materials Views, vol. 5, 2015, 23 pages.

Liu, S. et al., "Ferroelectric Domain Wall Induced Band Gap Reduction and Charge Separation in Organometal Halide Perovskites," Journal of Physical Chemistry Letters, vol. 6, 2015, pp. 693-699.

Nechache, R. et al., "Bandgap tuning of multiferroic oxide solar cells," Nature Photonics, vol. 9, Jan. 2015, pp. 61-67.

Nayak, P. et al., "Mechanism for rapid growth of organic-inorganic halide perovskite crystals," Nature Communications, vol. 7, 2016, 8 pages.

Quarti, C. et al., "Structural and optical properties of methylammonium lead iodide across the tetragonal to cubic phase transition: implications for perovskite solar cells," RSC Energy & Environmental Science, vol. 9, 2016, pp. 155-163.

Rakita, Y. et al., "Tetragonal Ch3Nh3PbI3 Is Ferroelectric," Proceedings of the National Academy of Sciences, vol. 114, 2017, 36 pages.

Rohm, H. et al., "Ferroelectric domains in methylammonium lead iodide perovskite thin-films," RSC Energy & Environmental Science, vol. 10, 2017, pp. 950-955.

Schulz, P. et al., "Interface energetics in organo-metal halide perovskite-based photovoltaic cells," RSC Energy & Environmental Science, vol. 7, 2014, pp. 1377-1381.

Scott, J. et al., "Ferroelectric Memories," Science, vol. 246, No. 4936, Dec. 15, 1989, pp. 1400-1405.

Sewvandi, G. et al., "Antiferroelectric-to-Ferroelectric Switching in $CH_3NH_3PbI_3$ Perovskite and Its Potential Role in Effective Charge Separation in Perovskite Solar Cells," Physical Review Applied, vol. 6, 2016, 11 pages.

Shelhas, L. et al., "Monitoring a Silent Phase Transition in $CH_3NH_3PbI_3$ Solar Cells via Operando X-ray Diffraction," ACS Energy Letters, vol. 1, 2016, pp. 1007-1012.

Sherkar, T. et al., "Can ferroelectric polarization explain the high performance of hybrid halide perovskite solar cells"?, RSC Phys. Chem. Chem. Phys., vol. 18, 2016, pp. 331-338.

Spanier, J. et al., "Power conversion efficiency exceeding the Shocklye-Queisser limit in a ferroelectric insulator," vol. 10, Sep. 2016, 8 pages.

Steirer, K. et al., "Defect Tolerance in Methylammonium Lead Triiodide Perovskite," ACS Energy Letters, vol. 1, 2016, pp. 360-366.

Strelcov, E. et al., "$CH_3NH_3PbI_3$ perovskites: Ferroelasticity revealed," Science Advances, Research Article, vol. 3, 2017, 8 pages.

Wei, J. et al., "Hysteresis Analysis Based on the Ferroelectric Effect in Hybrid Perovskite Solar Cells," Journal of Physical Chemistry Letters, vol. 5, 2014, pp. 3937-3945.

Yang, M. et al., "Enhancement of Local Photovoltaic Current at Ferroelectric Domain Walls in BiFeO3," Scientific Reports, Feb. 20, 2017, pp. 1-8.

Yang, S. Y. et al., "Above-bandgap voltages from ferroelectric photovoltaic devices," Nature Nanotechnology, vol. 5, Feb. 2010, pp. 143-147.

(56) References Cited

OTHER PUBLICATIONS

Ye, H. et al., "An Above-Room-Temperature Ferroelectric Organo-Metal Halide Perovskite: (3-Pyrrolinium)(CdCl$_3$)," Angewandte Communications, vol. 53, 2014, pp. 11242-11247.
Yuan, Y. et al., "Anomalous photovoltaic effect in organic-inorganic hybrid perovskite solar cells," Science Advances Research Article, Physical Science, vol. 3, 2017, 7 pages.
Xiao, z. et al., "Giant switchable photovoltaic effect in organometal trihalide perovskite devices," Nature Materials, vol. 14, Feb. 2015, 7 pages.
Zheng, F. et al., "First-principles calculation of bulk photovoltaic effect in CH3NH3PbI3 and $CH_3NH_3PbI_3-_xCl_x$," Journal of Physical Chemistry Letters, vol. 6, 2015, pp. 31-37.
Zhu, H. et al., "Screening in crystalline liquids protects energetic carriers in hybrid perovskites," Science Reports, vol. 353, Issue 6306, Sep. 2016, pp. 1409-1413.
Zhou, Y. et al., "Giant photostriction in organic-inorganic lead halide perovskites," Nature Communications, vol. 7, 2015, 8 pages.
PCT/US18/24140 Search Report dated Jun. 20, 2018, 3 pages.
PCT/US18/24140 Written Opinion dated Jun. 20, 2018, 5 pages.

\* cited by examiner

HYBRID PEROVSKITE BULK PHOTOVOLTAIC EFFECT DEVICES AND METHODS OF MAKING THE SAME

CROSS-REFERENCE TO RELATED APPLICATIONS

This application claims the benefit of U.S. Provisional Patent Application No. 62/476,492 filed Mar. 24, 2017, the contents of which are incorporated herein by reference in their entirety.

CONTRACTUAL ORIGIN

The United States Government has rights in this disclosure under Contract No. DE-AC36-08GO28308 between the United States Department of Energy and Alliance for Sustainable Energy, LLC, the Manager and Operator of the National Renewable Energy Laboratory.

BACKGROUND

Perovskite solar cells have shown remarkable progress in recent years with rapid increases in conversion efficiency, from initial reports of 2-3% in 2006 to 20% in 2015. Perovskite solar cells may offer the potential for an earth-abundant and low-energy-production solution to truly large-scale manufacturing of photovoltaic (PV) modules. While perovskite solar cells have achieved very high efficiencies in a very short amount of time, a number of challenges remain before perovskite solar cells can become a competitive commercial technology.

Although organic-inorganic perovskite materials have been studied for more than a century, initial studies on methylammonium lead halides for semiconductor applications, including thin-film transistors and light-emitting diodes, started in the last two decades. The first application of hybrid organic-inorganic perovskite absorbers in solar cells occurred in 2006. However, these early cells were of rather poor efficiency (<4%) due in part to the liquid electrolyte used, which limited both device stability and the open circuit voltage due to compromised interfacial chemistry and energetics. The application of a solid-state hole transport material (HTM), Spiro-MeOTAD (2,2',7,7'-tetrakis(N,N-di-p-methoxyphenylamine)-9,9'-spirobifluorene) improved the efficiency to 10% by 2012. Subsequent improvements in performance and stability have come through continued investigation of mixed halide perovskites, improved contact materials, new device architectures, and improved deposition processes, with 20% efficiency having been reported in late 2014. However, there remains a need for improved organic-inorganic perovskite compositions and materials to further improve the performances of devices fabricated from these materials so that they can successfully compete with incumbent materials, both from technical and economical perspectives.

SUMMARY

An aspect of the present disclosure is a composition that includes a perovskite crystal having a ferroelectric domain aligned substantially parallel to a reference axis. In some embodiments of the present disclosure, the perovskite crystal may include $ABX_3$, where A is a first cation, B is a second cation, and X is an anion. In some embodiments of the present disclosure, A may include an alkyl ammonium cation. In some embodiments of the present disclosure, B may include a metal element. In some embodiments of the present disclosure, the metal element may include lead. In some embodiments of the present disclosure, X may include a halogen. In some embodiments of the present disclosure, the perovskite crystal may include methylammonium lead iodide.

In some embodiments of the present disclosure, the ferroelectric domain may have a crystal structure that includes at least one of a tetragonal phase and/or an orthorhombic phase. In some embodiments of the present disclosure, the ferroelectric domain may be characterized by a Rayleigh response having a positive slope. In some embodiments of the present disclosure, the ferroelectric domain may be characterized by a $d_{33}$ measurement having a value greater than zero pC/N. In some embodiments of the present disclosure, the $d_{33}$ measurement may be between 0.1 pC/N and 10,000 pC/N.

An aspect of the present disclosure is device that includes a layer that includes a perovskite crystal that includes a ferroelectric domain aligned substantially parallel to a reference axis, where the perovskite crystal includes $ABX_3$, where A is a first cation, B is a second cation, and X is an anion. In some embodiments of the present disclosure, the layer may further include a first surface and a second surface, the second surface may be substantially parallel to the first surface, the first surface and the second surface may define a thickness of the layer, and the reference axis may be substantially perpendicular to the first surface and the second surface. In some embodiments of the present disclosure, the thickness may be between 1 Å and 10 mm. In some embodiments of the present disclosure, the ferroelectric domain may have a length between 1 Å and 10 mm. In some embodiments of the present disclosure, the device may further include a first electrode that includes a first metal positioned against the first surface and a second electrode that includes a second metal positioned against the second surface, where the layer is positioned between the first electrode and the second electrode. In some embodiments of the present disclosure, the first metal and the second metal may be the same.

An aspect of the present disclosure is a method that includes applying a gradient to a perovskite crystal having a characteristic length, where the applying creates at least one ferroelectric domain within the perovskite crystal, the ferroelectric domain has a crystal structure that is not in a cubic phase, and the ferroelectric domain is aligned substantially parallel with the characteristic length. In some embodiments of the present disclosure, the applying may include at least one of applying an electric field gradient and/or a temperature gradient across the characteristic length. In some embodiments of the present disclosure, the applying the electric field gradient may include applying a voltage between 1 mV and 100 V across the characteristic length.

BRIEF DESCRIPTION OF THE DRAWINGS

Some embodiments are illustrated in referenced figures of the drawings. It is intended that the examples and figures disclosed herein are to be considered illustrative rather than limiting.

FIG. 4A illustrates the PFM small signal amplitude response trace (solid line) and retrace (dashed line). FIG. 4B illustrates the PFM small signal phase response trace (solid line) and retrace (dashed line). FIG. 4C illustrates an image of a single crystal of MAPbI$_3$ with natural faceting before metallization. FIG. 4D illustrates the Rayleigh response, determined from the EAc response of the permittivity measured at 1 MHz, from the lowest applied signal ($9.2 \times 10^{-4}$ kV/cm) increasing with applied voltage to the maximum ($7.6 \times 10^{-3}$ kV/cm); arrow indicates increasing applied EAC. The Rayleigh response decreases with increasing temperature, collapsing near the global phase transition temperature for the cubic phase, which is an indication of the presence of ferroelectricity. FIG. 4E illustrates a schematic of the material structure, the temperature dependence of the global phase transitions, possible mechanisms of structural modification, and Rayleigh response in MAPbI$_3$.

FIG. 5A illustrates the Rayleigh coefficient, a calculated from the data in FIG. 4D, as a function of temperature. FIG. 5B illustrates dielectric loss measurements taken concurrently with the Rayleigh analysis indicating a decrease in Vac dependence above the global phase transition temperature. The arrow indicates increasing Applied EAc, from a low value of $9.2 \times 10^{-4}$ kV/cm to a high value of $7.6 \times 10^{-3}$ kV/cm FIG. 6A illustrates large voltage PFM amplitude and FIG. 6B illustrates PFM phase. FIG. 6C illustrates optical microscope image of crystal surface after poling showing stable periodic domain lines which extend across the face of the crystal.

FIG. 7A illustrates XPS measurements of the I 3d core level region. FIG. 7B illustrates XPS measurement of the Pb 4f core level region. The top traces correspond to poled crystals and the bottom traces correspond to unpoled crystals.

FIG. 8A illustrates AFM topography of domain lines, area delineated by dashed line corresponds to the electric force microscopy (EFM) amplitude scan area shown in FIG. 8B in at 8V bias. FIG. 8C illustrates line scans corresponding to the solid line in FIG. 8A, showing the response for topography (dashed line, right axis), EFM amplitude signal at 0V bias (dotted line, left axis) and 8V (solid line, left axis). FIG. 8D illustrates AFM topography image and line scan (FIG. 8E) after aging a poled crystal for 3 weeks in ambient conditions.

FIG. 9A illustrates the permittivity over a range of frequencies shows dispersion that decreases with increasing temperature above the global phase transition temperature. FIG. 9B illustrates the concurrently measured dielectric loss as a function of temperature and frequency.

REFERENCE NUMBERS

Figure 1:
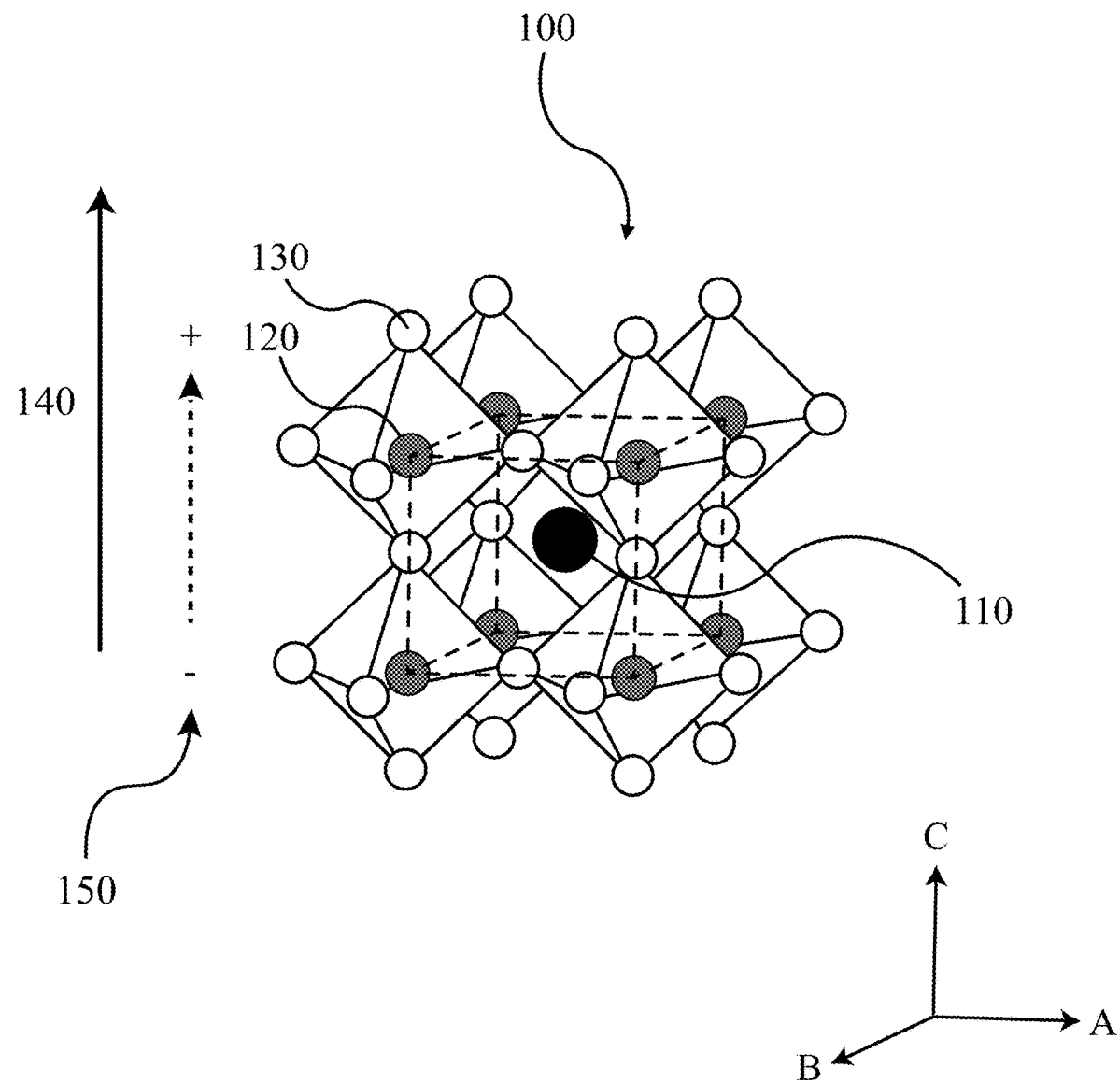
FIG. 1 illustrates a perovskite crystal structure, according to some embodiments of the present disclosure.

100 . . . perovskite
110 . . . A-cation
120 . . . B-cation
130 . . . X-anion
140 . . . driving mechanism
150 . . . first dipole
155 . . . second dipole
200 . . . device
210 . . . perovskite layer
220 . . . first ferroelectric domain
225 . . . second ferroelectric domain
227 . . . non-ferroelectric domain
230 . . . current collector
300 . . . method
310 . . . depositing
315 . . . perovskite film
320 . . . treating
325 . . . perovskite layer
330 . . . applying
335 . . . final perovskite layer

DETAILED DESCRIPTION

The present disclosure may address one or more of the problems and deficiencies of the prior art discussed above. However, it is contemplated that some embodiments as disclosed herein may prove useful in addressing other problems and deficiencies in a number of technical areas. Therefore, the embodiments described herein should not necessarily be construed as limited to addressing any of the particular problems or deficiencies discussed herein.

The present disclosure relates to ferroelectricity in organic-inorganic perovskite materials (e.g. single crystals of methyl ammonium lead iodide) and methods for making such materials, as well as the use of ferroelectric domain engineering to control the electronic response in these materials. A comprehensive set of methodologies including temperature dependent Rayleigh analysis, piezoresponse force microscopy, and d$_{33}$ Berlincourt piezoelectric measurements have resulted in experimental results, described herein, that confirm relaxor ferroelectricity with nanoscale domain ordering. As will be described in more detail below, the ferroelectric response of the organic-inorganic perovskite materials studied exhibited sharp declines above 57° C., which is consistent with the tetragonal-to-cubic phase transition temperature. Large signal poling greater than 16 V/cm induced permanent macroscopic ferroelectric domains (up to 40 µm wide, and between 0.01 mm and 1 mm in length), which demonstrated preferential stabilization over a period of weeks and a distinguishable domain specific electronic response. The impact of the ferroelectric domains on the opto-electronic response was characterized through X-ray photoemission spectroscopy (XPS), and electric force microscopy (EFM). The XPS results indicate a rigid shift of 400 meV in the binding energy of the iodine and lead core level peaks in the poled crystal with respect to the unpoled crystal. Additionally, there is a domain specific electrical response seen by EFM. The ability to control the ferroelectric response provides routes to increase both device stability and improve photovoltaic performance through domain engineering, and provides key insights for future designs of novel, high-efficiency photovoltaic materials. The ability to control the ferroelectric domain orientation allows for the development of bulk photovoltaic effect devices, which employ the ferroelectric polarization to separate photogenerated charge carriers.

FIG. 1 illustrates that a perovskite 100, including an organic-inorganic perovskite, may organize into cubic crystalline structures and may be described by the general formula $ABX_3$, where X (130) is an anion and A (110) and B (120) are cations, typically of different sizes with the A-cation 110 typically larger than the B-cation 120. In a cubic unit cell, the B-cation 120 resides at the eight corners of a cube, while the A-cation 110 is located at the center of the cube and with 12 X-anions 130 centrally located between B-cations 120 along each edge of the unit call. Typical inorganic perovskites include calcium titanium oxide (calcium titanate) minerals such as, for example, $CaTiO_3$ and $SrTiO_3$. In some embodiments of the present invention, the A-cation 110 may include a nitrogen-containing organic compound such as an alkyl ammonium compound. The B-cation 120 may include a metal and the X-anion 130 may include a halogen. Although FIG. 1 illustrates a perovskite having a cubic crystalline structure, a perovskite may have other crystalline structures, including tetragonal or orthorhombic (e.g. I4 cm). In some embodiments of the present disclosure, a perovskite 100 may include at least a first portion that is substantially in the cubic crystalline phase and a second portion that is substantially in a different crystalline phase, e.g. tetragonal, orthorhombic. In some embodiments of the present disclosure, a perovskite may have a combination of more than one crystal phase, for example a mixture of a cubic phase and a tetragonal phase and/or orthorhombic phase.

Additional examples for an A-cation 110 include organic cations and/or inorganic cations. A-cations 110 may be an alkyl ammonium cation, for example a $C_{1-20}$ alkyl ammonium cation, a $C_{1-6}$ alkyl ammonium cation, a $C_{2-6}$ alkyl ammonium cation, a $C_{1-5}$ alkyl ammonium cation, a $C_{1-4}$ alkyl ammonium cation, a $C_{1-3}$ alkyl ammonium cation, a $C_{1-2}$ alkyl ammonium cation, and/or a $C_1$ alkyl ammonium cation. Further examples of organic A-cations 110 include methylammonium ($CH_3NH^{3+}$), ethylammonium ($CH_3CH_2NH^{3+}$), propylammonium ($CH_3CH_2CH_2NH^{3+}$), butylammonium ($CH_3CH_2CH_2CH_2NH^{3+}$), formamidinium ($NH_2CH=NH^{2+}$), and/or any other suitable organic compound. In other examples, an A-cation 110 may include an alkylamine. Thus, an A-cation 110 may include an organic component with one or more amine groups, or transition metal cations. For example, an A-cation 110 may be an alkyl diamine such as formamidinium $(CH(NH_2)_2)^+$.

Examples of metal B-cations 120 include, for example, lead, tin, germanium, and or any other 2+ valence state metal that can charge-balance the perovskite 100. In some embodiments of the present disclosure, a metal B-cation 120 may have a 1+, 2+, 3+, or 5+ valence state, for example at least one of Na, K, Ba, Sr, Ca, Pb, Bi, Sn, and/or In. Examples for the X-anion 130 include halogens: e.g. fluorine, chlorine, bromine, iodine and/or astatine. In some cases, a perovskite 100 may include more than one X-anion 130, for example pairs of halogens; chlorine and iodine, bromine and iodine, and/or any other suitable pairing of halogens. In other cases, the perovskite 100 may include two or more halogens of fluorine, chlorine, bromine, iodine, and/or astatine. In some embodiments of the present disclosure, at least one X-anion 130 may be mixed with oxygen.

Thus, the A-cation 110, the B-cation 120, and the X-anion 130 may be selected within the general formula of $ABX_3$ to produce a wide variety of perovskites 100, including, for example, methylammonium lead triiodide ($CH_3NH_3PbI_3$), and mixed halide perovskites such as $CH_3NH_3PbI_{3-x}Cl_x$ and $CH_3NH_3PbI_{3-x}Br_x$. Thus, a perovskite 100 may have more than one halogen element, where the various halogen elements are present in none integer quantities; e.g. x is not equal to 1, 2, or 3. In addition, perovskite halides, like other organic-inorganic perovskites, can form three-dimensional (3-D), two-dimensional (2-D), one-dimensional (1-D) or zero-dimensional (0-D) networks, possessing the same unit structure.

As stated above, the A-cation 110 may include organic constituents in combination with each other. In some cases, the organic constituent may be an alkyl group such as straight-chain and/or branched saturated hydrocarbon group having from 1 to 20 carbon atoms. In some embodiments, an alkyl group may have from 1 to 6 carbon atoms. Examples of alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like.

Referring again to FIG. 1, and without wishing to be bound by theory, the application of a driving mechanism 140 in a particular orientation and/or direction, for example an electric field, appears to result in a structural reorientation (e.g. displacement of the center ion) within the perovskite 100 unit cell. In the example of FIG. 1, the driving mechanism 140 is substantially parallel to the A-axis and results in at least a partial reorientation of the elements of the perovskite (cations and/or anions) along the A-axis, which further results in the alignment of charges within the perovskite. This alignment of charges creates a dipole 150 of at least some of the perovskite elements in three-dimensional (3D) space, as defined by the unit cell between the centers of the B-cation 120 octahedra, which is referred to herein as "polling". Thus, depending on the driving mechanism 140 used, and the alignment of its forces in 3D space, a perovskite 100 may form a dipole 150 of its elements aligned along the A-axis, B-axis, and/or C-axis, and aligned substantially parallel with the driving mechanism 140. In FIG. 1, the driving mechanism 140, e.g. an electric field, is shown to be substantially parallel to the C-axis, which results in the formation of a dipole 150 also substantially parallel with the C-axis. Polycrystalline materials, with crystal symmetries may accommodate the structural changes by re-orienting along the closest direction to the applied field. Regions where the structural distortions and the dipole 150 orient along the same axis and direction are referred to herein as "ferroelectric domains", which may vary in size from two unit cells on the order of Angstroms, up to millimeters in length. Similar poling may be produced by driving mechanisms 140 such as at least one of strain, strain gradients, temperature gradients, and/or electric field gradients. The range of applied poling voltages may be between 1 mV and 100 V. A temperature gradient as a driving mechanism 140 may be between 50° C./micrometer and 200° C./micrometer. In some embodiments, the temperature gradient may be pulsed at regular time intervals. Thus, the application of an appropriate driving mechanism 140, e.g. electric field, may result in the alignment of at least one of an A-cation 110, a B-cation 120, and/or an X-anion 130 along an axis that is substantially parallel to at least one of the A-axis, the B-axis, and/or the C-axis, resulting in the creation of a dipole 150 and the creation of at least one ferroelectric domain positioned within the perovskite 100. These structural changes may also result in subsequent changes in at least one of an electrical, an optical, and/or a mechanical property. In some examples of the present disclosure, a perovskite material containing ferroelectric domains, treated according to at least some of the embodiments described herein, will exhibit the BPE response, a piezoelectric response, and birefringence, as demonstrated herein. The poling may remain oriented along the same direction after the driving mechanism is removed unless the material reaches some condition that provides enough energy (e.g. a temperature above the Curie temperature) that the material may rearrange and reassume a less-poled, less-ferroelectric state.

Figure 2:
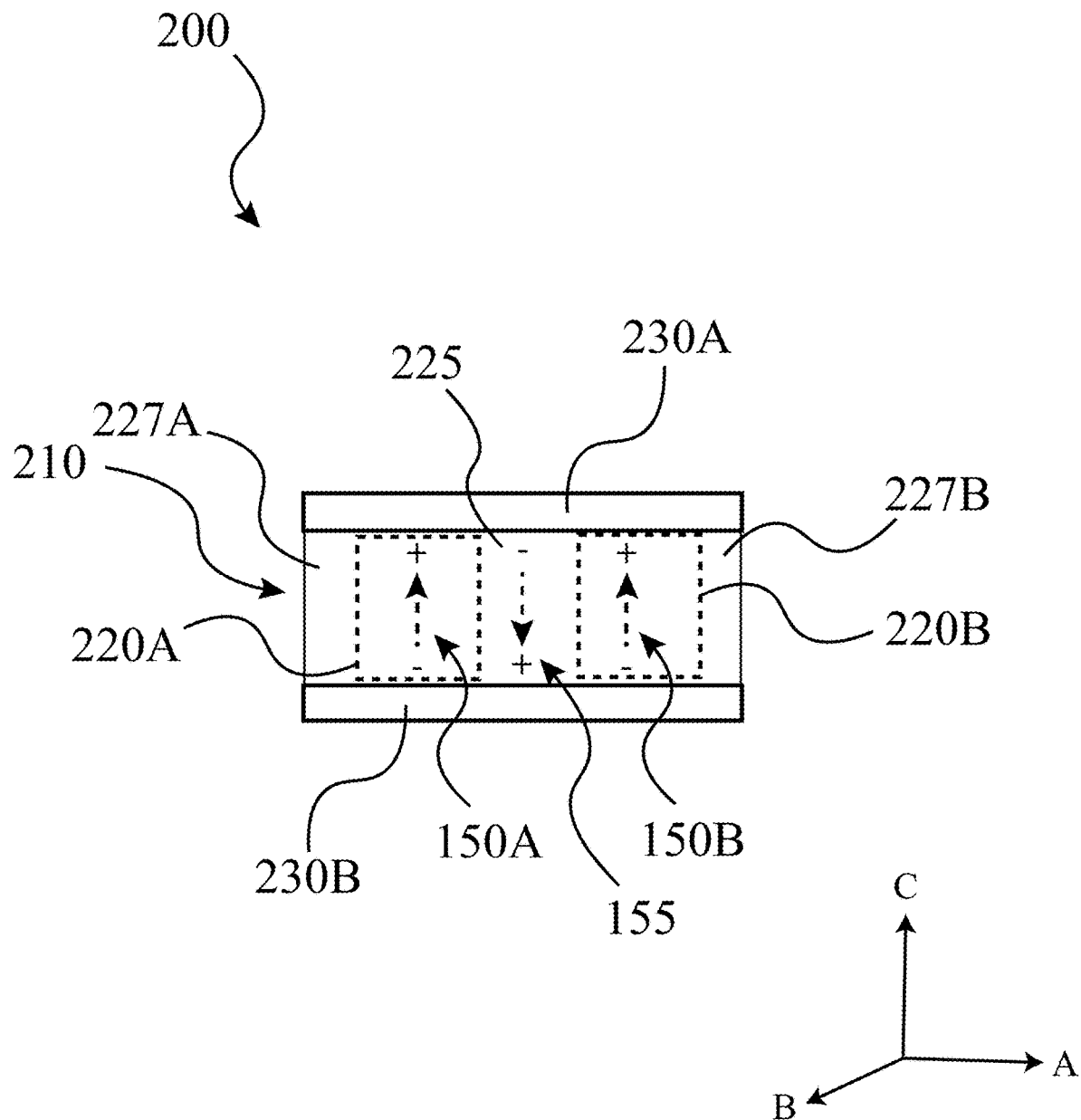
FIG. 2 illustrates a device that includes a perovskite having ferroelectric domains, according to some embodiments of the present disclosure.

FIG. 2 illustrates a device 200, for example a solar cell, that includes a perovskite layer 210 having a first dipole 150 (two shown; 150A and 150B) aligned along a dimension of the perovskite layer 210; e.g. aligned parallel to the perovskite layer 210 thickness dimension. In the example of FIG. 2, the first dipole (150A and 150B) forms a first ferroelectric domain (two shown; 220A and 22B), represented by dashed rectangles spanning the entirety of the thickness of the perovskite layer 210. However, it should be understood that in some embodiments of the present disclosure, a perovskite layer 210 may have one or more ferroelectric domains. For example, at least one first ferroelectric first domain (220A and/or 220B) may be separated by non-ferroelectric domains (227A and 227B) and/or by at least one second ferroelectric domain 225 have a second dipole 155 oriented in a different and/or opposite direction relative to the first dipole (150A and 150B) of the first ferroelectric domain (220A and 220B). In some embodiments of the present disclosure, two or more ferroelectric domains (e.g. 220A, 220B, and/or 225) may have intersecting areas or volumes such that a single ferroelectric domain results; e.g. having no intervening, non-ferroelectric domains 227. Thus, a ferroelectric domain (220A, 220B, and/or 225) may be characterized by a thickness dimension that is substantially parallel its respective dipole (150A, 150B, and/or 155) (e.g. along the C-axis of FIG. 2), where the thickness dimension may be between several Angstrom and several millimeters; e.g. the thickness dimension of a ferroelectric domain (220A, 220B, and/or 225) may be between 1 Å and 100 millimeters, or between 10 Å and 10 millimeters, or between 100 Å and 1 millimeter. A ferroelectric domain (220A, 220B, and/or 225) may also have a characteristic width dimension (B-axis) and length dimension (A-axis), both of which may be at least orders of magnitude larger than the thickness dimension (C-axis) of the ferroelectric domains (220A, 220B, and/or 225). In addition, FIG. 2 illustrates the ferroelectric domains (220A, 220B, and/or 225) as being rectangular in shape. However, this is for illustrative purposes only and a ferroelectric domain (220A, 220B, and/or 225) may have any geometric shape, which may be defined by the starting shape of the perovskite layer 210 and/or the conditions used during the formation of the ferroelectric domain (220A, 220B, and/or 225).

Thus, as shown herein, a device may include a perovskite (e.g. layer) having at least one ferroelectric domain. In addition, the perovskite (e.g. layer) may have a least one non-ferroelectric domain. The ferroelectric domain may be identified by the presence of a dipole, whereas the non-ferroelectric domain may lack a measurable dipole. The presence of the dipole of a ferroelectric domain, and conversely, the absence of a dipole in a non-ferroelectric domain, may be identified using the analytical methods described herein, which include Rayleigh analysis, polarization-electric field loops, $d_{33}$ Berlincourt measurements, PFM, EFM, contact Kelvin probe force microscopy (cK-PFM), scanning microwave impedance microscopy (sMIM), and/or visual inspection (e.g. optical microscopy). According to some of the embodiments described herein, the presence or absence of ferroelectric domains in a perovskite material (e.g. layer) may be indicated as summarize below in Table 1.

TABLE 1

Ferroelectric versus Non-Ferroelectric Indicators

| Method | Measures | Ferroelectric | Non-Ferroelectric | See Figure |
|---|---|---|---|---|
| Rayleigh | C(Vac) | Positive slope. | Flat or negative slope. | 4D, 5A, 5B |
| Polarization-Electric Field | P(E) = I(V) | Square in the second and fourth quadrant, hysteresis, pointy ends, discontinuous slope. | straight line, circle. | NA |
| $d_{33}$ | strain induced charge | Between 0.1 pC/N and 10,000 pC/N ($d_{33}$ > 0 pC/N). | No piezoelectric response, or no difference in response after poling in opposite direction. | NA |
| EFM | dC/dV, Voltage | Linearly segregated areas with distinct electrical response, change in surface charge buildup. | No difference, topographic induced differences. | 8A, 8B, 8C |
| PFM | Displacement (Vdc) | Positive displacement, linear, hysteresis, crossing response at x = 0. | No displacement, or quadratic displacement at high voltages. | 4A, 4B, 6A, 6B |
| cKPFM | surface charge build-up | Two separate bands. | single band. | 11 |
| visual/SEM | — | Observable surface domains. | No clear delineation. | 6C |
| sMIM | dI/dV | At V = 0, I ≠ 0 | At V = 0, I = 0 | NA |

The device 200 of FIG. 2 also includes a first current collector 230A and a second current collector 230B, such that the device 200 may function as a bulk photo effect device. The bulk photovoltaic effect (BPE) is the separation of photogenerated charges due to the asymteric wavefunction of the material, which in this case is provided by the coherent structural distortion within a ferroelectric domain, (and the difference in-built potential between and through ferroelectric domains). Open current voltages greater than the band gap may result from BPE. Any asymmetric material with a band gap may exhibit the BPE. Unlike a traditional solar cell, a BPE device does not require a junction, but instead, can utilize a single layer of active (ferroelectric) material. A BPE solar cell will be much different from a conventional p-n junction solar cell in a few key areas. For example, a BPE solar cell may utilize a band gap in the visible spectrum and it may generate a photo voltage and current much like a conventional solar cell. However, the photo voltage of BPE solar cell is not limited by the bang gap such that open-circuit voltages on the kiloVolt magnitude are possible. In addition, the transport mechanisms in a BPE device may be ballistic resulting in faster transport and higher efficiencies. Although FIG. 2 illustrates a device 200 that may be a solar cell, other devices utilizing perovskite films having ferroelectric domains are contemplated and are considered within the scope of the present disclosure (e.g. transistors, sensors, energy harvesters, ferroelectric-random access memory, opto-electronics). In addition, the device 200 of FIG. 2 may include other elements (e.g. layers) typically found within solar cells, for example, additional perovskite layers (e.g. designed to absorb light of different wavelengths).

Figure 3:
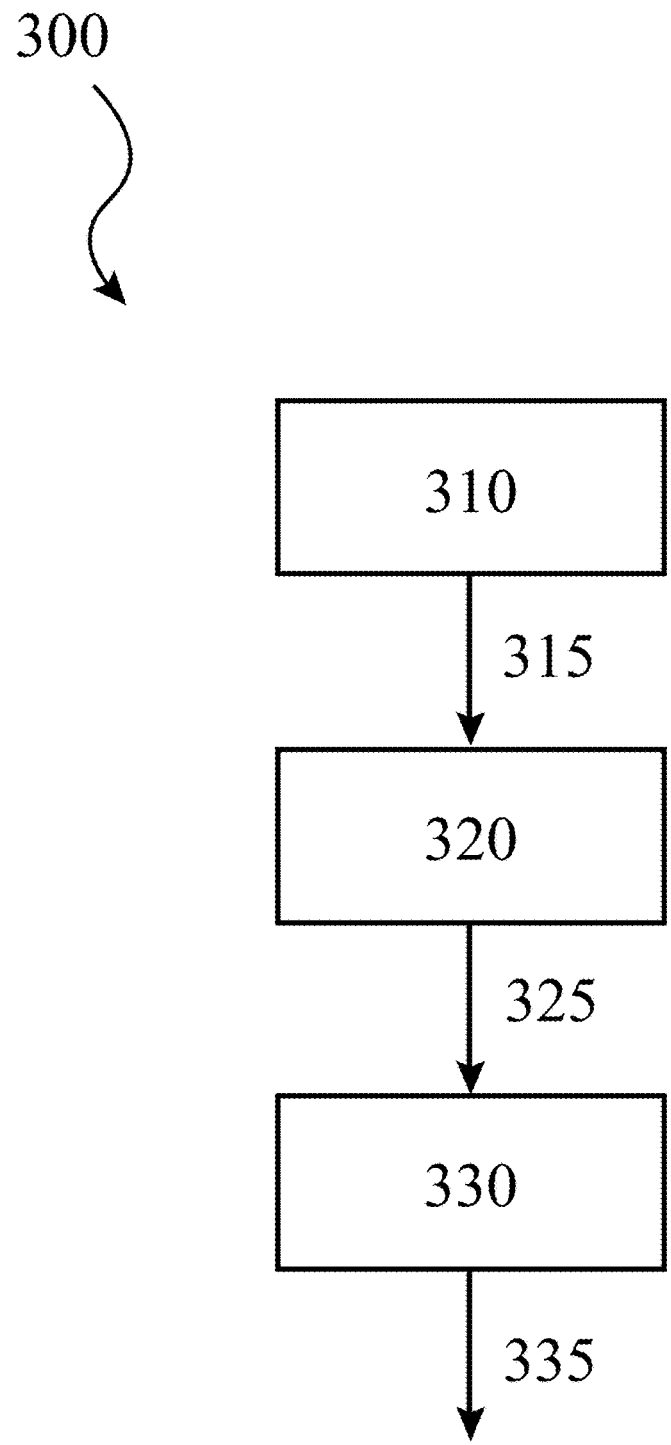
FIG. 3 illustrates a method for producing a perovskite having ferroelectric domains, according to some embodiments of the present disclosure.

FIG. 3 illustrates a method 300 for making a final perovskite layer 335 having ferroelectric domains. The method 300 may begin with the depositing 310 of a perovskite film 315, for example the depositing of a perovskite film 315 by a solution method onto a substrate, according to methods known to one having skill in the art. The perovskite film 315 may transformed into a solid perovskite layer 325 by treating 320 the perovskite film 315. For example, the treating 320 may include heating the perovskite film 315 to a temperature between 20° C. and about 200° C. At this point, the perovskite film 315 may not contain a dipole or a ferroelectric domain. These may be formed by the subsequent applying 330 of a driving mechanism (e.g. poling), for example an electric field, resulting in the formation of a final perovskite film 315 having at least one ferroelectric domain. An electric field may be applied to a perovskite material by positioning the perovskite material between a first electrode and a second electrode and applying a voltage across the two electrodes. In some embodiments of the present disclosure, the applying 330 and the treating 320 may be performed substantially simultaneously. For the example of an electric field driving mechanism, the electric field may be applied during the heating of the perovskite film 315, such that the ferroelectric domains form as the perovskite transitions from a liquid solution to a solid. For the example of an electric field driving mechanisms, an electric field having a voltage between greater than 0 V and 100 V may be applied for a time period of between 1 second and 1000 seconds, or between 1 second and 100 seconds, or between 1 second and 10 seconds, while below, above or at room temperature, and along the [001] family of planes. As used herein, room temperature is defined to be between 15° C. and 25° C.

The work present herein unequivocally confirms that $MAPbI_3$, with a near ideal band gap of 1.6 eV and verified solar cell efficiency over 19%, can be ferroelectric. These results run counter to the current prevailing view that ferroelectricity does not occur in $MAPbI_3$, which has come about in part due to the difficulties in making definitive measurements using conventional techniques, especially on thin film samples. These previous results highlight the importance of developing appropriate methods in order to detect a ferroelectric response in semiconducting ferroelectrics. The ability to control the ferroelectric response is also demonstrated herein, which allows for the exploitation of benefits unique to ferroelectrics, such as increasing the material stability and controlling the opto-electronic properties through domain engineering and creating a BPE device.

Figure 4A:
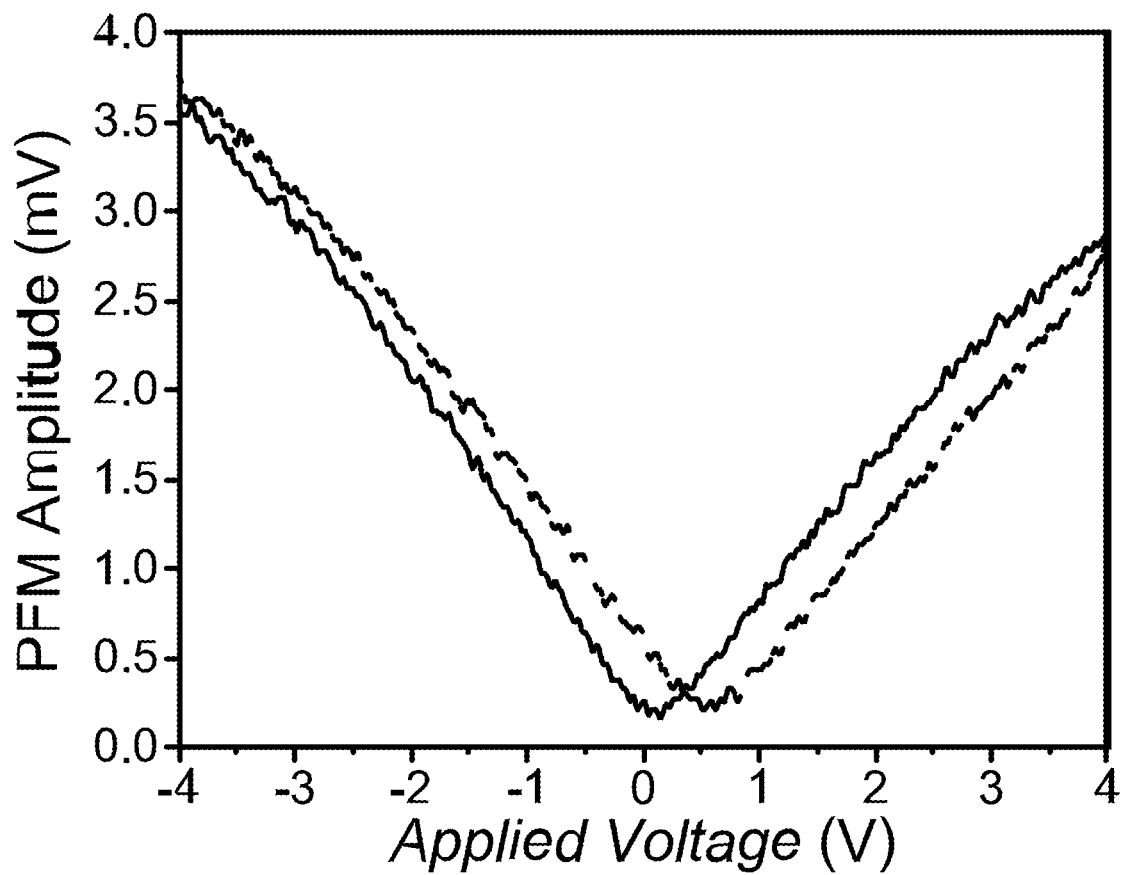
FIGS. 4A-4E illustrate piezoresponse force microscopy (PFM) and temperature dependent ferroelectric response in large, high-quality MAPbI$_3$ single crystals, according to some embodiments of the present disclosure.
Figure 4B:
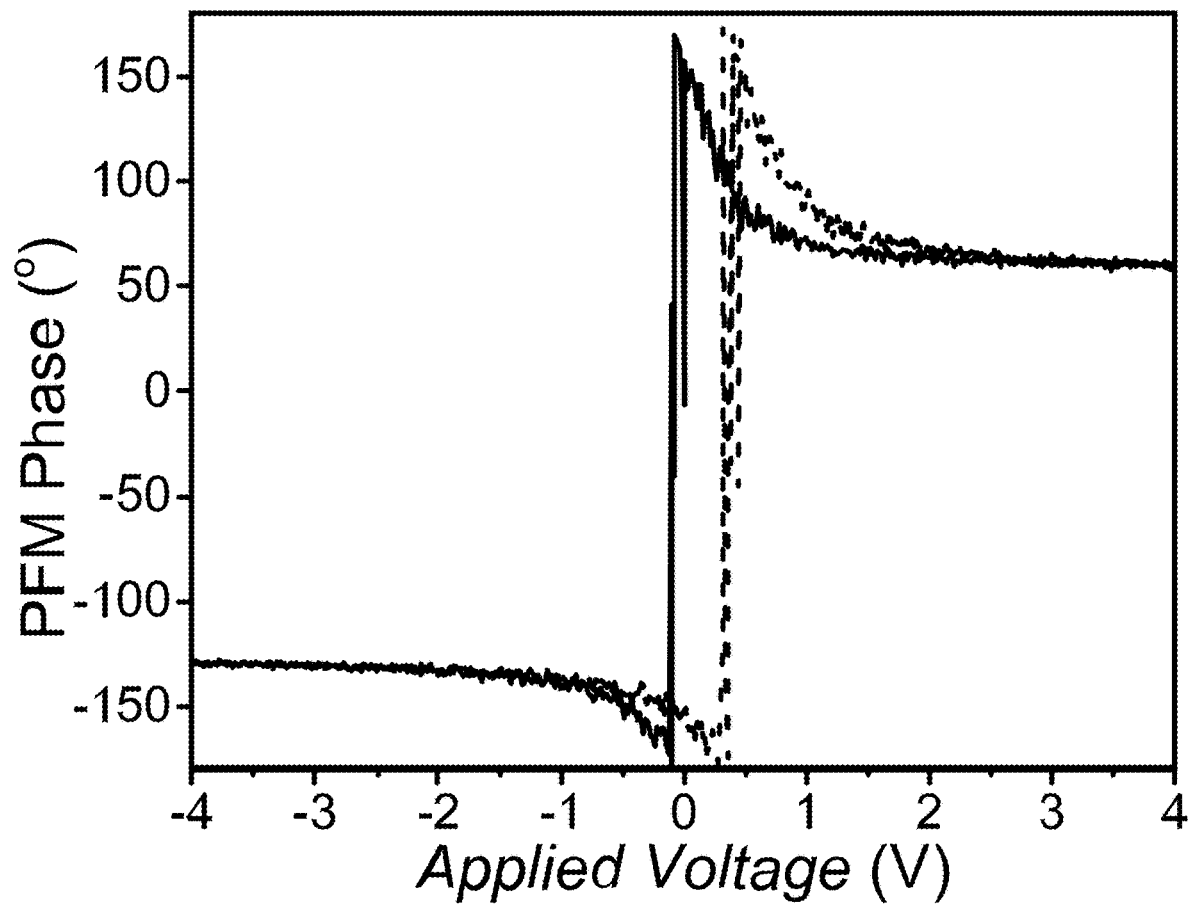
Figure 4C:
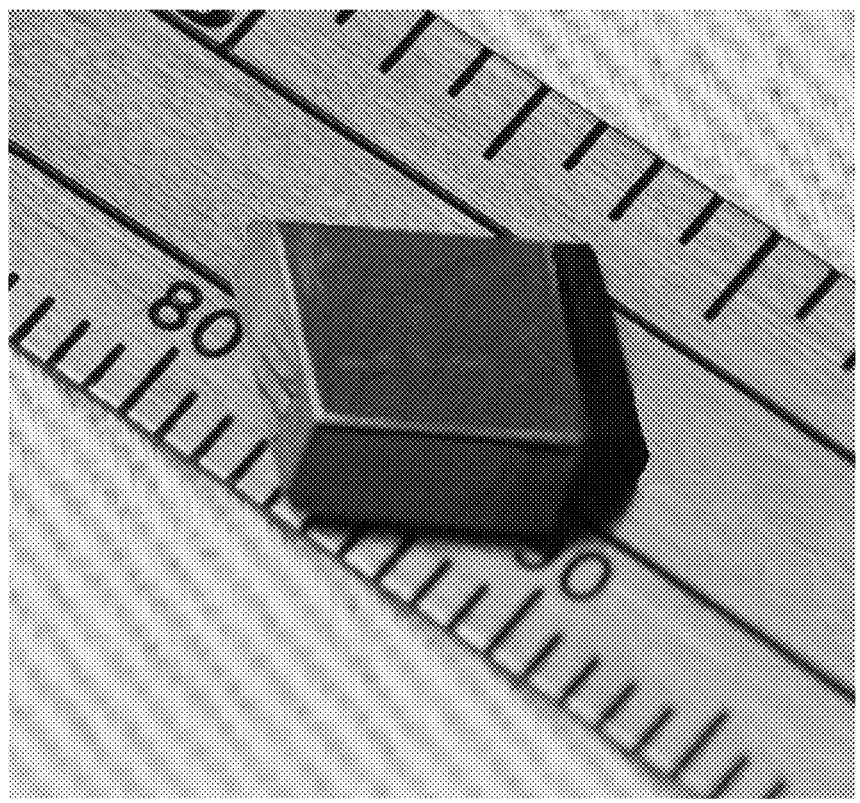

As described herein, high quality single crystals and unique small signal electrical measurements were utilized to definitively confirm ferroelectricity in $MAPbI_3$. The characterization techniques employed to confirm the ferroelectric response included: temperature dependent Rayleigh analysis, dielectric measurements, piezoresponse force microscopy, electric force microscopy (EFM), and $d_{33}$ Berlincourt piezoelectric measurements. After identifying a ferroelectric response and determining the conditions for macroscopic domain control, the impact of poling on the material stability and electrical response were measured through EFM and X-ray photoemission spectroscopy (XPS), Piezoelectricity is a prerequisite of ferroelectricity, making piezoresponse force microscopy (PFM) an effective initial screening method for ferroelectricity in $MAPbI_3$ single crystals. FIGS. 4A and 4B show representative PFM amplitude and phase as a function of applied VDc. The offset minimum in the forward and reverse sweeps, the linear displacement with applied field, and the hysteresis in trace and retrace are indicative of a piezoelectric (rather than a pure electrostrictive) response associated with the reorientation of ferroelectric domains by an electric field. The concomitant phase shift of 180° is congruent with ferroelectric domain reversal. This fulfills the criteria of ferroelectricity, a spontaneous polarization that can be reoriented with the application of an electric field. Identifying a ferroelectric response and showing polarization reorientation under an electric field in polycrystalline thin films through large signal, small area PFM scans is problematic due to the convolution of electrostatic, electrostrictive, and topographic contributions to the signal. These issues were avoided herein by utilizing smaller signal (160 V/cm, <4V), large electrode area static PFM scans, making it unlikely that the response is field-induced. If the material was only piezoelectric, or electrostrictive, then no minimum offset, no significant hysteresis, and no phase shift would occur. Hence, the PFM data strongly supports ferroelectricity and the narrow hysteresis is indicative of ferroelectric ordering on the nanoscale, e.g. relaxor ferroelectricity.

Figure 4D:
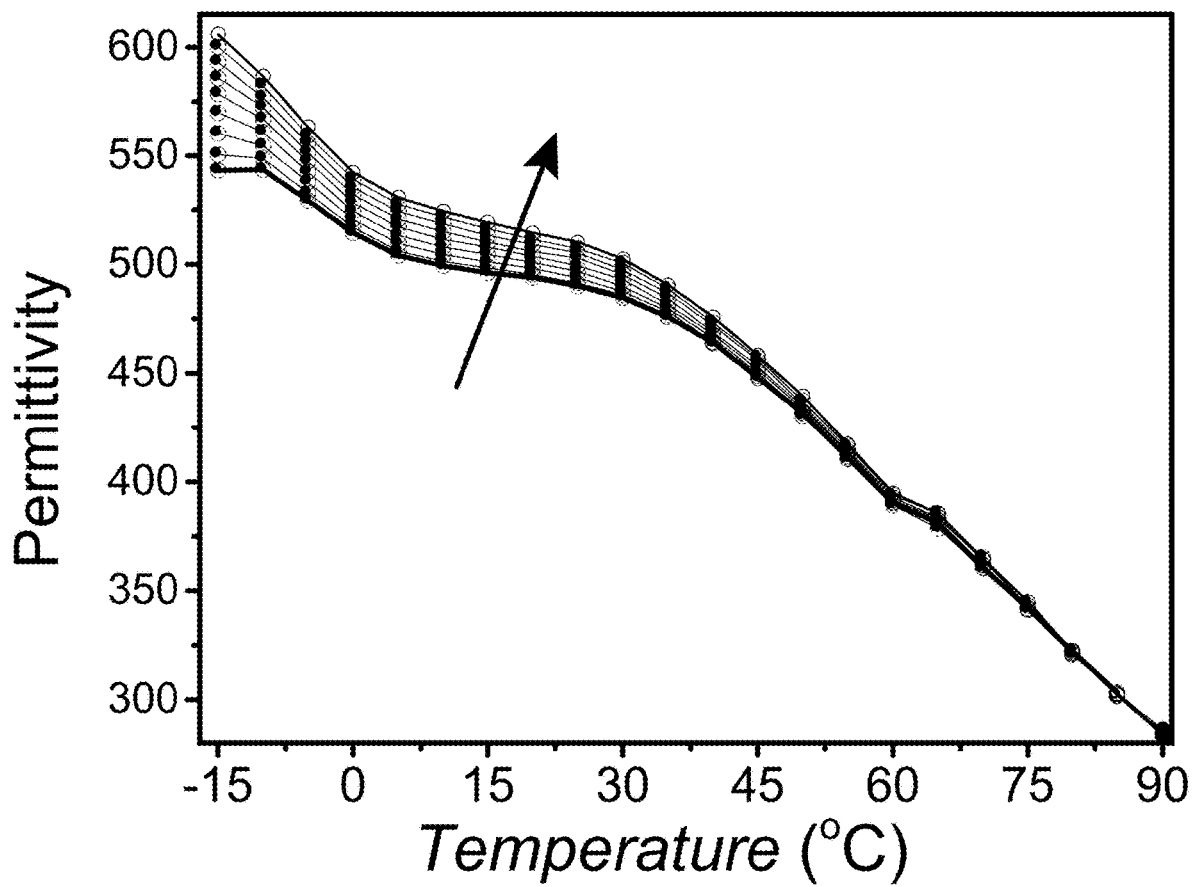
Figure 4E:
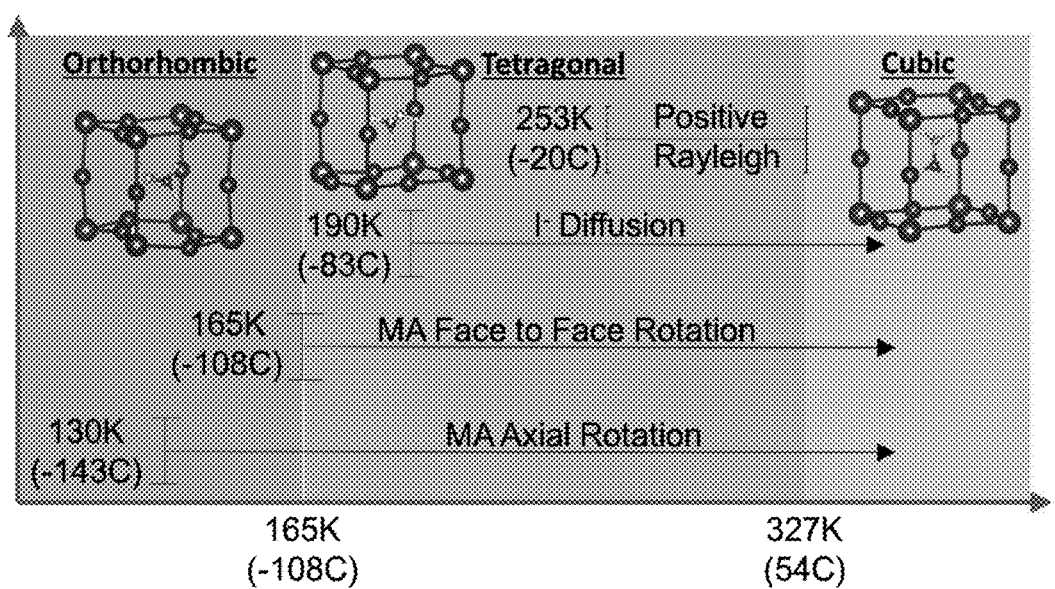
Figure 5A:
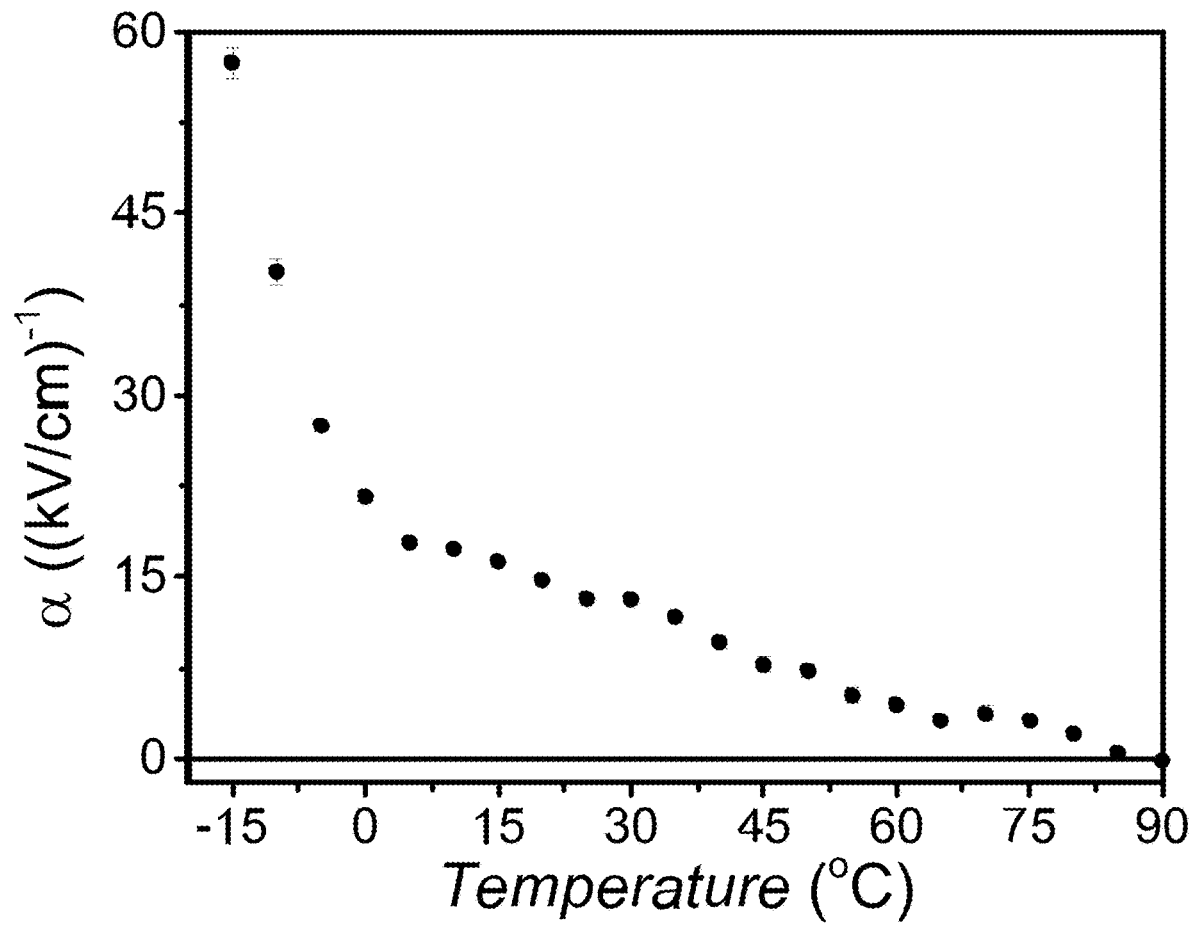
FIGS. 5A and 5B illustrate Rayleigh coefficient and dielectric loss tangent for a single crystal MAPbI$_3$ at 1 MHz, according to some embodiments of the present disclosure.
Figure 5B:
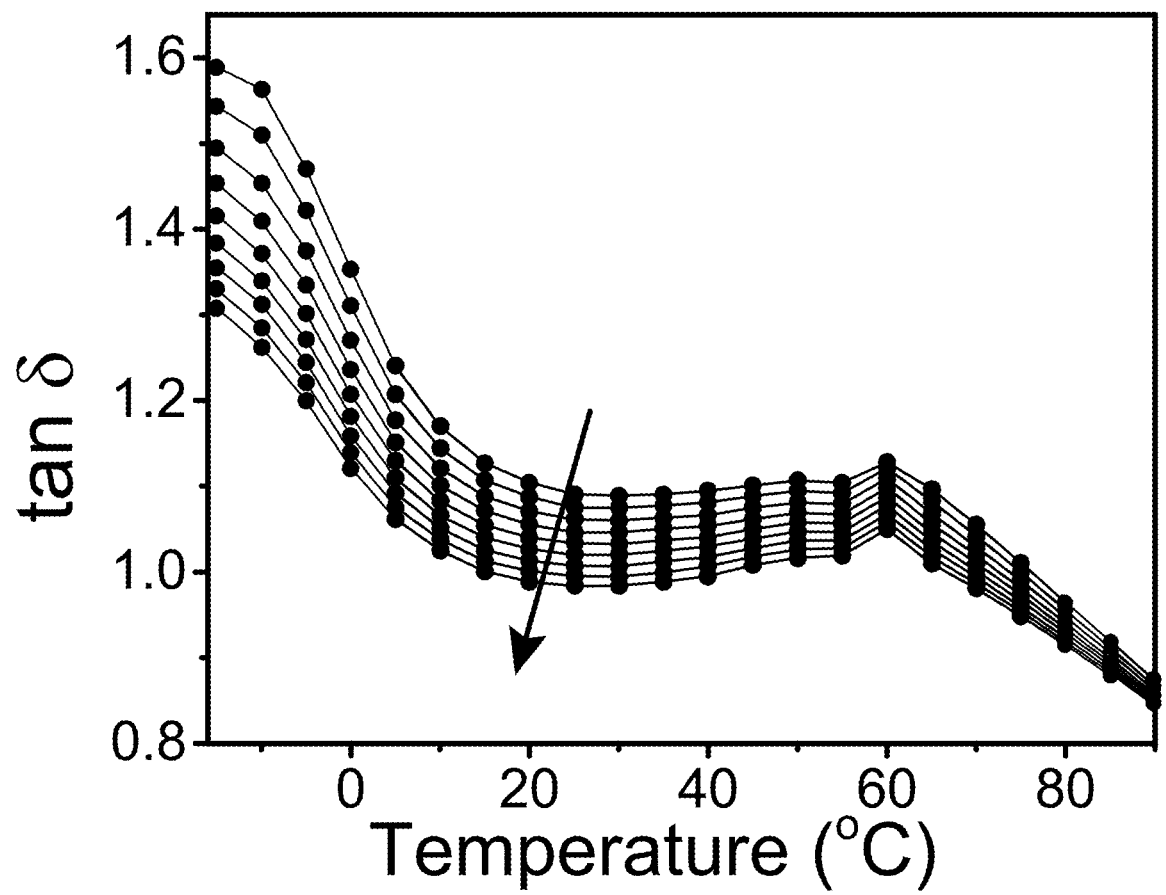

Although PFM and PE loops are the most commonly reported ferroelectric measurements, these methods are sensitive to small changes in charge such that the movement of free charge can overwhelm the ability to see a ferroelectric response and are thus problematic in semiconducting material Advanced alternative methodologies based on Rayleigh analysis were also employed in the work described herein. The Rayleigh response is the linear change in permittivity under an applied electric field, EAC, due to the irreversible movement of domain walls, domain clusters, or phase boundaries. Rayleigh analysis can be used as an indicator for the presence of ferroelectric domain wall movement with a Gaussian distribution of restoring forces. FIG. 4D shows the EAC induced dielectric response measured under small signal conditions (<8.3 V/cm, <2V) at 1 MHz with increasing temperature. The Rayleigh coefficient and concurrent loss are shown in FIGS. 5A and 5B. A clear Rayleigh response is apparent in MAPbI$_3$, indicating ferroelectric polar clusters, with mobile boundaries. This response decays with increasing temperature, sharply declining near 57° C., and finally disappearing beyond 75° C. The transition near 57° C. is consistent with previous reports of the temperature of transition between the tetragonal and cubic phase between 54° C. and 60° C. The persistence of the Rayleigh response beyond the global phase transition temperature is a common characteristic of a relaxor ferroelectric, indicating that a few local polarized regions remain above the global phase transition temperature. The decrease in the loss tangent above the transition temperature indicates that the response is not dominated by ion movement and that there is a contribution from the ferroelectric response The nano-polar regions in a relaxor ferroelectric can be transitioned into a macroscopic ferroelectric state with an applied electric field in a process called poling. Poling was confirmed through direct Berlincourt measurements of the d$_{33}$ piezoelectric coefficient. Prior to the application of an electric field no piezoelectric response could be measured. After five minutes of poling at 21 V/cm, the d$_{33}$ was found to be 54 pC/N. The measured d$_{33}$ likely underestimates the actual piezoelectric response due to leakage currents, low applied poling voltages, and imperfect impedance. Interestingly, the DFT calculations of the piezoelectric tensor of MAPbI$_3$ are approximately an order of magnitude smaller than the experimental results. Note that the computational method has been compared to other piezoelectric materials in the literature and typically reproduces the measured response at an accuracy of +/−25%.

Figure 6A:
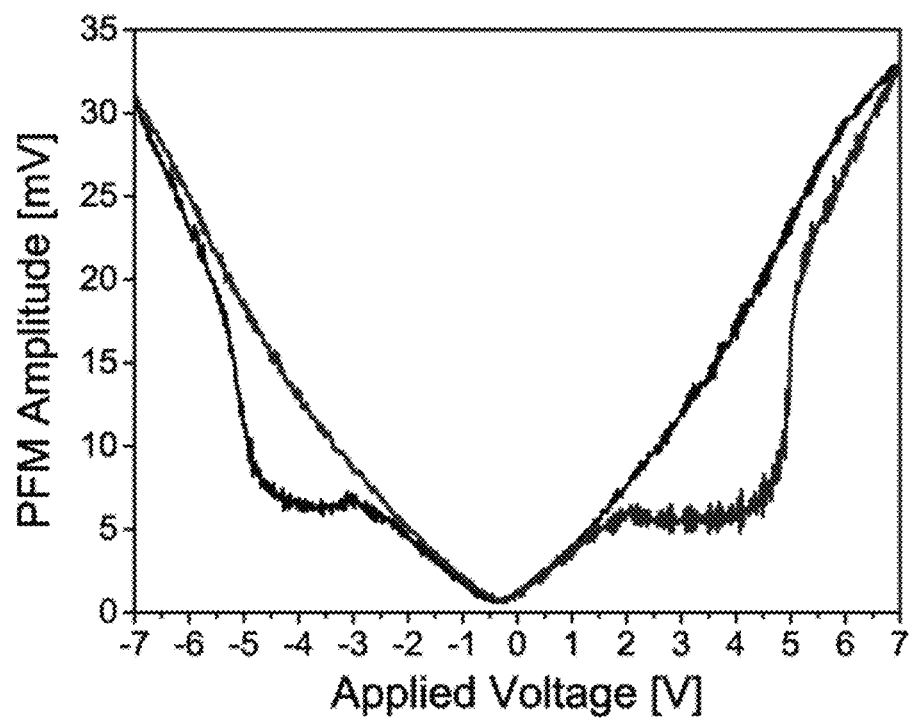
FIGS. 6A, 6B, and 6C illustrate poling induced macroscopic ferroelectric domains, according to some embodiments of the present disclosure.
Figure 6B:
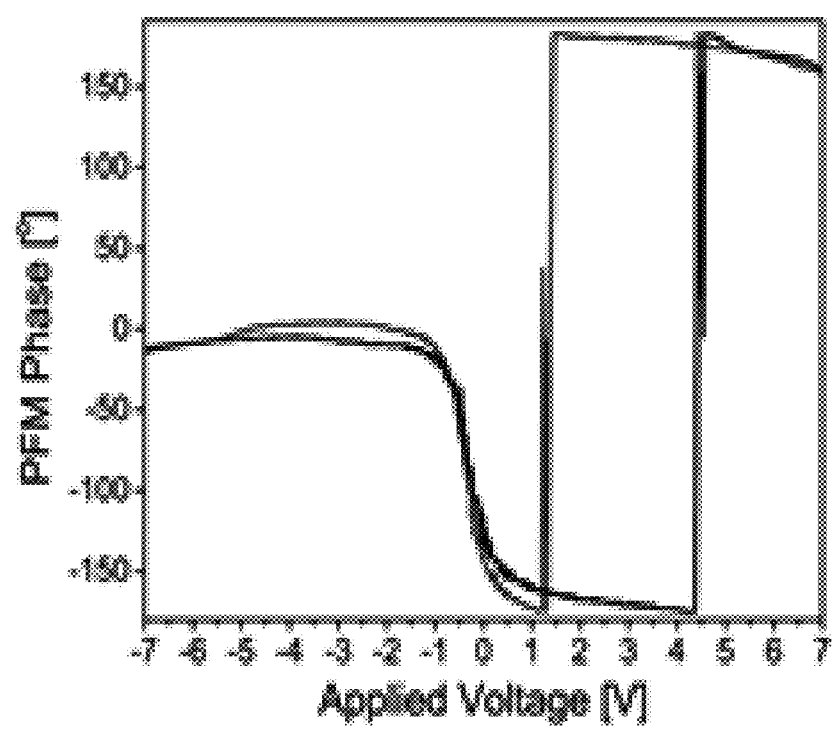
Figure 6C:
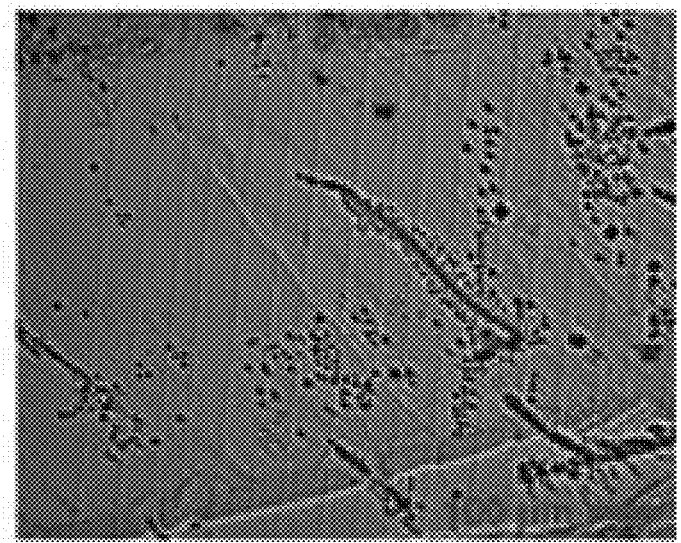

In addition to verifying the presence of ferroelectricity, the ability to pole the material into persistent macroscopic domains indicates that domain engineering can be used to select for a desired predominant polarization orientation and thus control the structure and electronic response. FIGS. 6A and 6B show the large signal PFM amplitude and phase. Simply stated, these data show the forward trace and backward trace for PFM amplitude and phase. The fact that the forward trace and backward trace do not fall directly on each other for the entire duration indicate the presence ferroelectric domains in the perovskite. The development of hysteresis with increasing electric field above 12 V/cm is consistent with a transition from the slim relaxor ferroelectric response into an induced macroscopic ferroelectric structure. After removing the applied bias large visible domain structures remained. Periodic domain structures extended millimeters across the surface of the samples, with domain widths that varied with poling field and orientation, ranging from between 2 µm and 40 µm, shown in FIG. 6C.

Figure 7A:
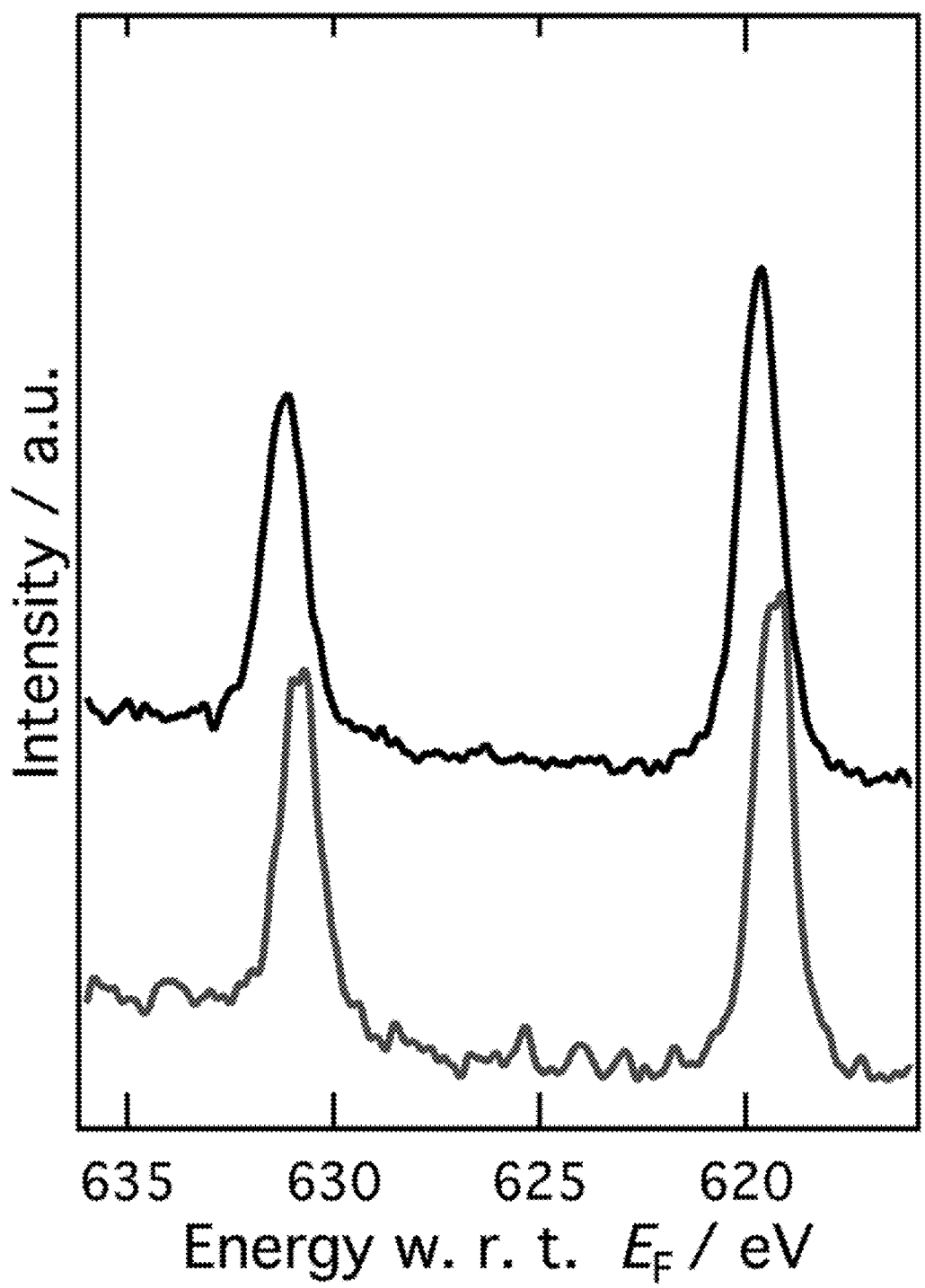
FIGS. 7A and 7B illustrate various properties of perovskite-containing devices, according to some embodiments of the present disclosure.
Figure 7B:
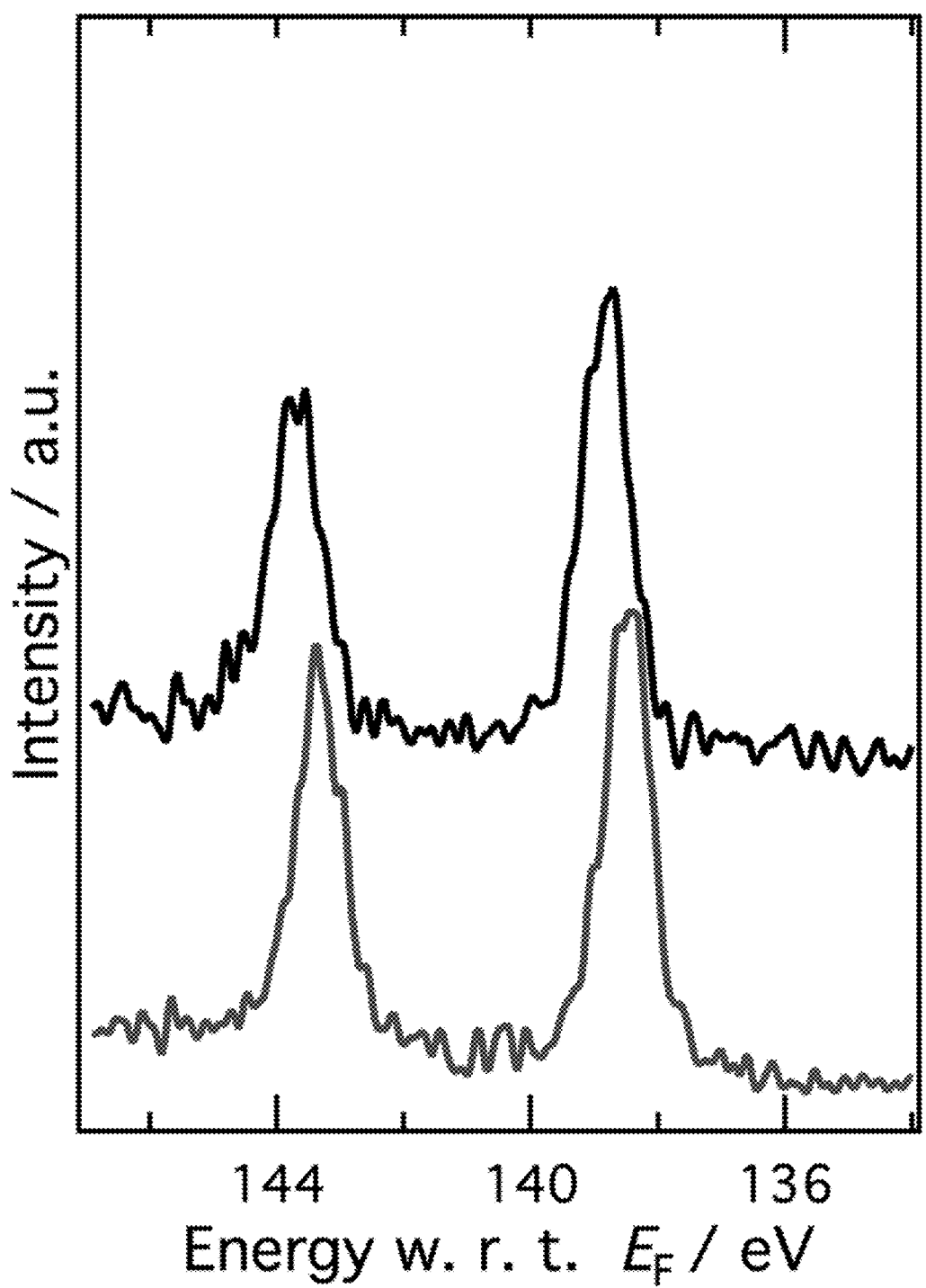

XPS was used to examine the impact of ferroelectricity on the electronic structure. The lead and iodine core level spectra of a poled and unpoled MAPbI$_3$ crystal are depicted in FIGS. 7A and 7B. Referring to FIG. 7A, for the unpoled crystal (bottom trace), the main I 3d$_{5/2}$ peak is centered at 619.3 eV which is consistent with an intrinsic response. Relative to the measurements taken on an unpoled crystal, the iodine core level peaks in the poled crystal exhibit a rigid shift in binding energy of 400 meV with a similar shift in the Pb 4f peaks (see FIG. 7B and Table 2 below). This change in Fermi level, E$_F$, position could be associated with sampling over domains that are predominantly oriented in such a way that there is a net electric field resembling a positively charged surface. These shifts could be indicative of a change in Fermi level position that suggests dipole doping.

TABLE 2

Centroid positions of lead and iodine core level peaks before and after poling

|  | Unpoled | Poled |
| --- | --- | --- |
| I 3d$_{5/2}$ | 619.3 eV | 619.7 eV |
| I 3d$_{3/2}$ | 630.8 eV | 631.2 eV |
| Pb 4f$_{7/2}$ | 138.5 eV | 138.9 eV |
| Pb 4f$_{5/2}$ | 143.3 eV | 143.7 eV |

While XPS provides specifics of the electronic structure, the macroscopic influence of ferroelectricity by performing EFM on poled crystals was also probed. These results strongly support the potential for a bulk photovoltaic response in this material and indicate the influence of ferroelectricity on the opto-electronic response.

Figure 8A:
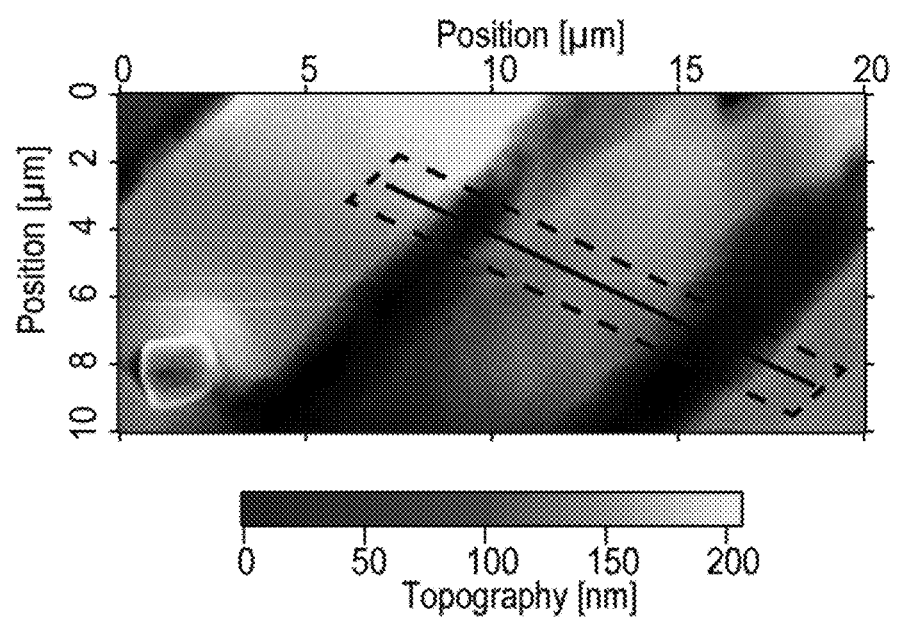
FIGS. 8A-8E illustrate various properties of perovskite-containing devices, according to some embodiments of the present disclosure.
Figure 8B:
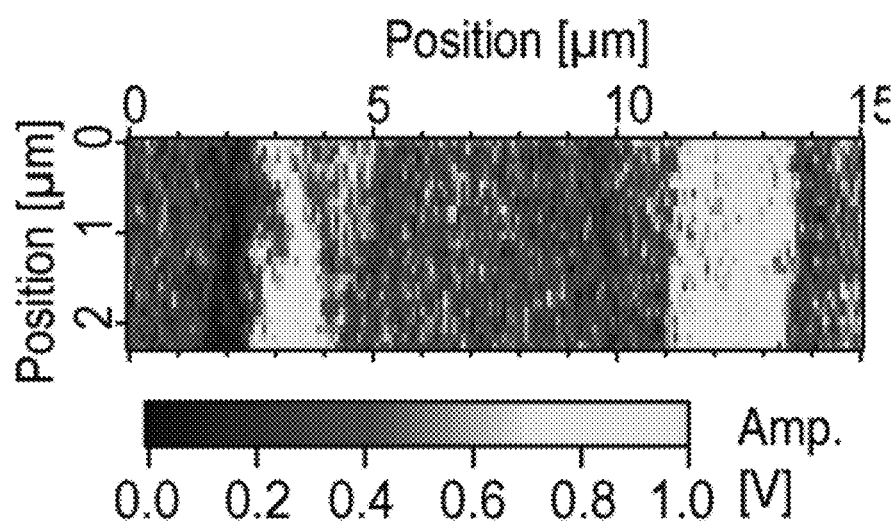
Figure 8C:
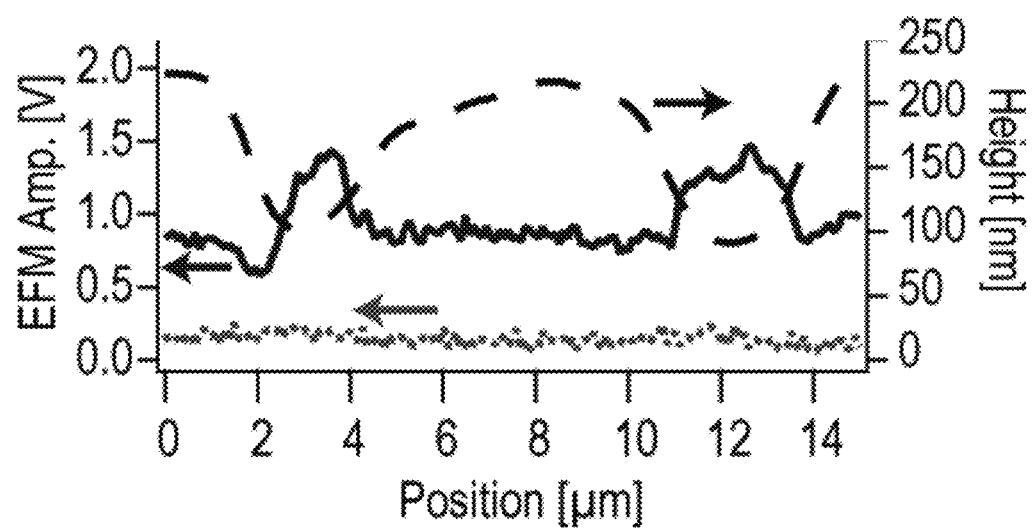
Figure 8D:
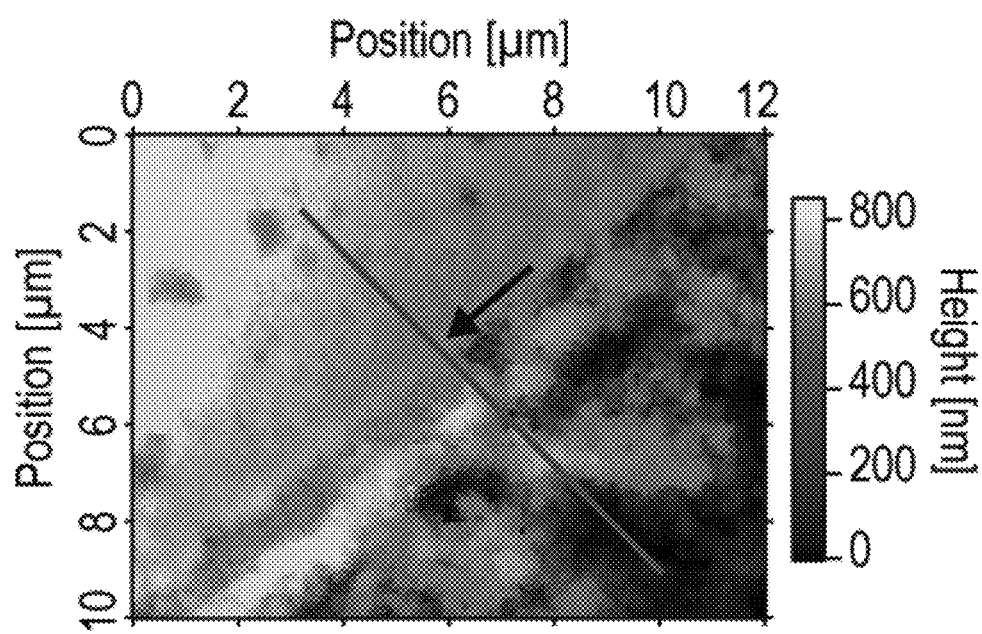
Figure 8E:
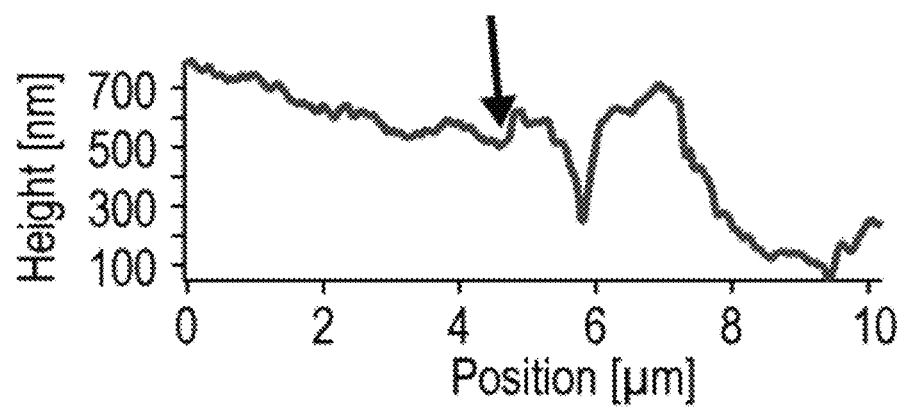

The domain specific response was investigated through EFM. It is shown that domains of differing orientations exhibit a measurably different electrical response. FIGS. 8A and 8B show the results of both the topographical and EFM scans. The 0V, 8V and topographical line scans are shown in FIG. 8C; the 0V scan shows no response verifying that the measured EFM signal is a function of a varied electrical response, and not due to topographical features or surface chemical potential differences. In contrast, the 8V scan shows a specific electrical response that is coincident with the domain structures. Although a complete analysis and understanding of the EFM response is beyond the scope of this work, it clearly demonstrates domain-specific electrical response, which, in turn, implies that a built-in field can be engineered into working devices. The difference in chemical potential at the surface of different domains plays a large role in the stability of the material over time. The EFM/AFM images taken after a period of intentional etching in air for a month showed that domains in the dominant orientation remained relatively unchanged while preferential etching and degradation occurred in domains with the opposite orientation. This effect is shown in FIGS. 8D and 8E with the arrow indicating the domain boundary. By poling a crystal or film along this preferential direction the stability of the material could be increased. Observing these phenomena in MAPbI$_3$ highlights a route to increase the material and device stability and reliability of the material over time via targeted domain design.

Using a broad range of unique characterization techniques across multiple length scales the existence of ferroelectricity in single crystals of MAPbI$_3$ is confirmed by the work described herein. An important implication of this work is that any ferroelectric semiconductor, like MAPbI$_3$, may also exhibit the bulk photovoltaic effect. The bulk photovoltaic effect in ferroelectrics relies on the spontaneous polarization, which enables efficient separation of photo-excited charge carriers without a p-n junction. This work shows that MAPbI$_3$ is ferroelectric, that the polarization can be controlled through polling, and that the domain structure impacts the opto-electronic response, three critical criteria for the development of BPE devices. These results support the idea that the BPE effect in MAPbI$_3$ may contribute to the spectacular photovoltaic response observed in this material.

Figure 9A:
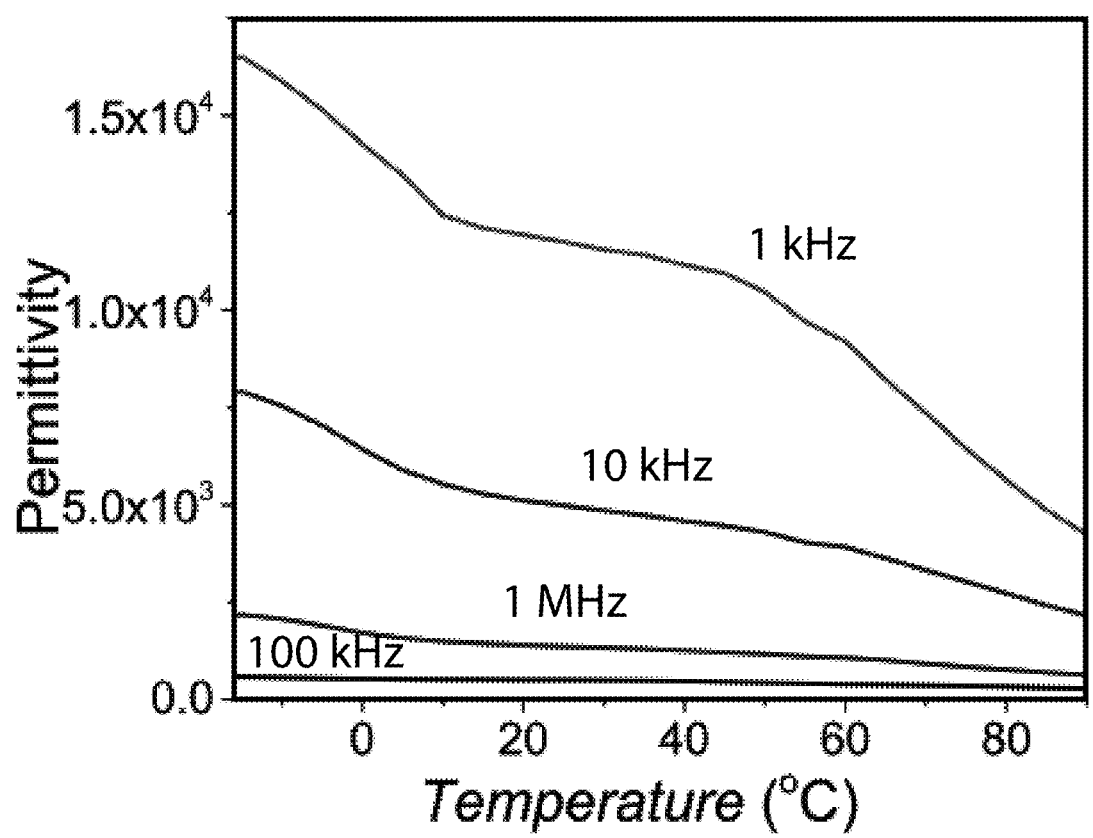
FIGS. 9A and 9B illustrate the dielectric response of single crystal MAPbI$_3$ as a function of temperature and frequency, according to some embodiments of the present disclosure.
Figure 9B:
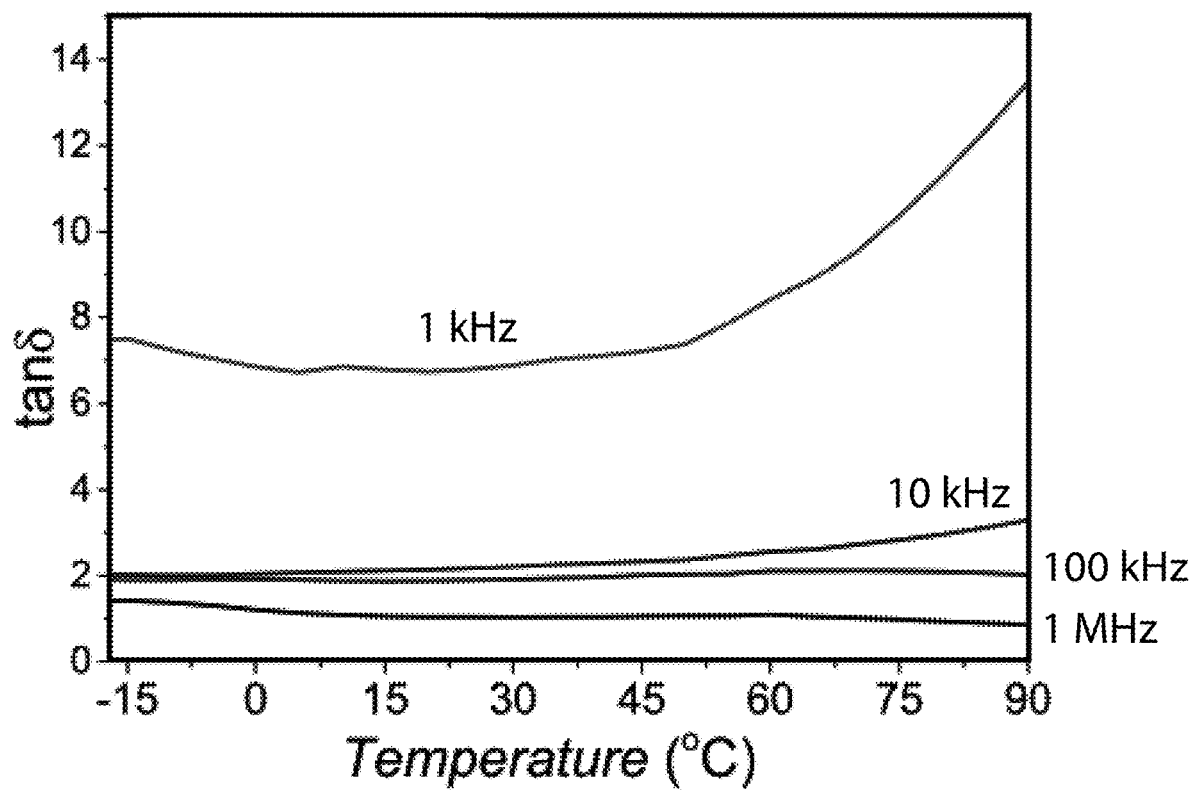

FIGS. 9A and 9B illustrate the dielectric response of single crystal MAPbI$_3$ as a function of temperature and frequency, according to some embodiments of the present disclosure. FIG. 9A illustrates the permittivity over a range of frequencies shows dispersion that decreases with increasing temperature above the global phase transition temperature. FIG. 9B illustrates the concurrently measured dielectric loss as a function of temperature and frequency.

Figure 10:
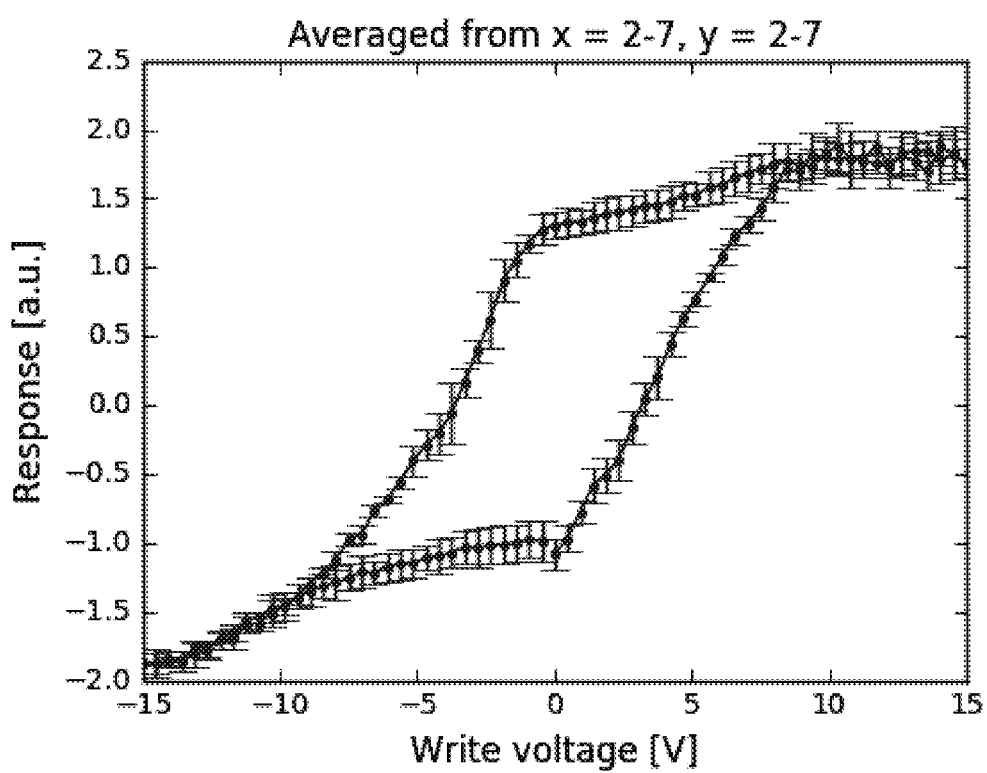
FIG. 10 shows the piezoresponse (taken as the band excitation-PFM amplitude multiplied by the cosine of BE-PFM phase response) as a function of applied voltage, according to some embodiments of the present disclosure.

FIG. 10 shows the piezoresponse (taken as the band excitation-PFM amplitude multiplied by the cosine of BE-PFM phase response) as a function of applied voltage on a single crystal of methylammonium lead iodide. This measurement is the average response over ten areas on the sample. The sharp saturated response, with square corners and low injected charge are indicative of a ferroelectric response.

Figure 11:
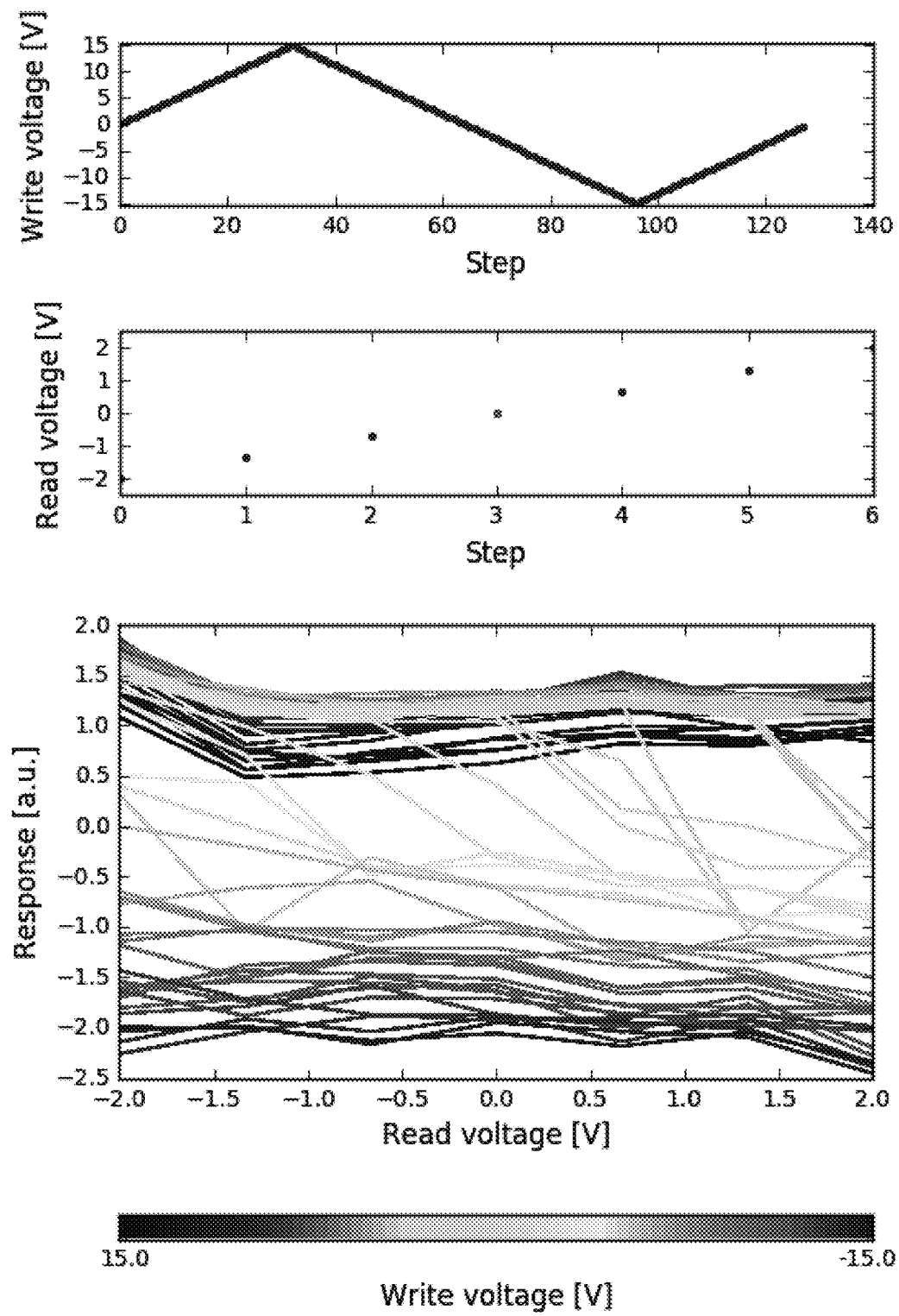
FIG. 11 illustrates the read/write voltage steps used in the BE-PFM experiment, according to some embodiments of the present disclosure.

FIG. 11 illustrates the read/write voltage steps used in the BE-PFM experiment (top two panels), the lower panel shows the measured, non-averaged response demonstrating the separation into two separate bands indicating a ferroelectric response.

Figure 12:
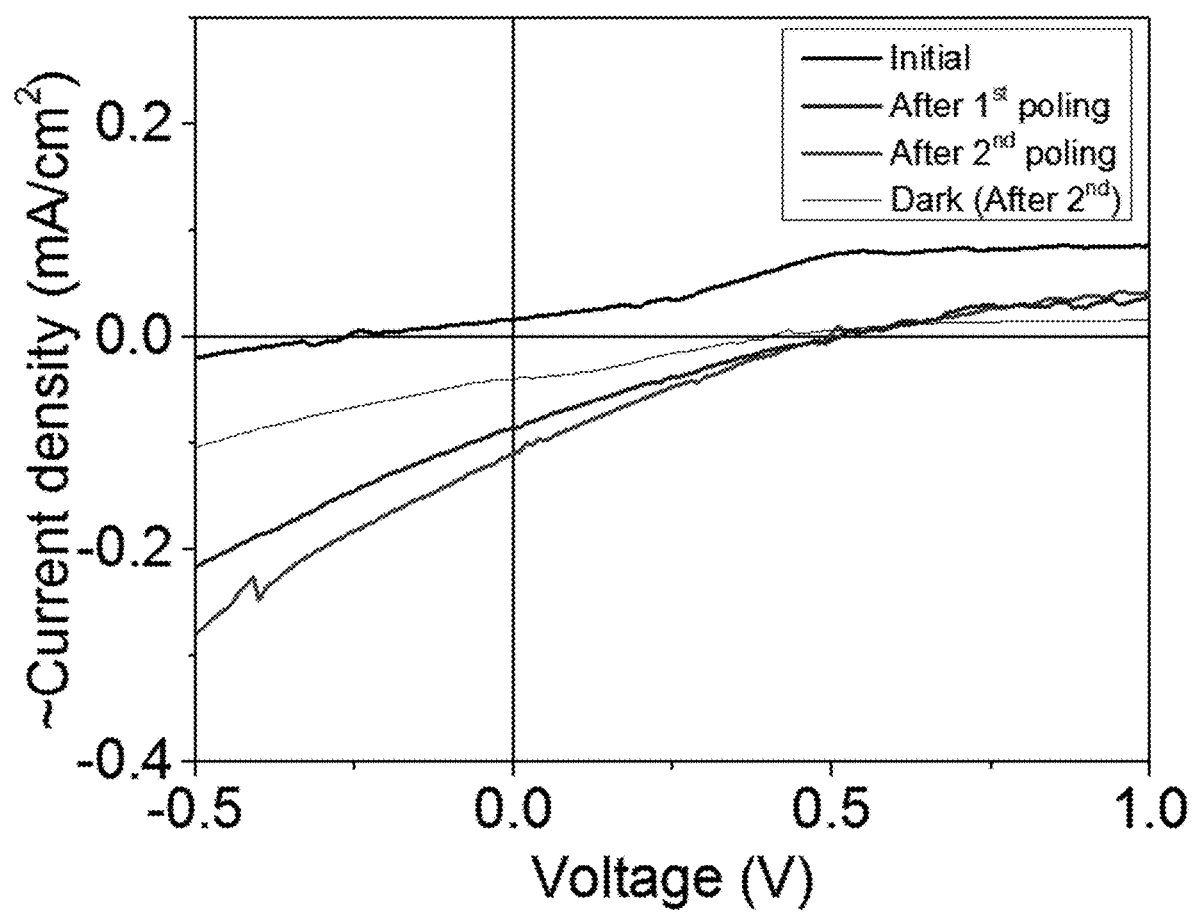
FIG. 12 illustrates the dC/dV response of a BPE device, according to some embodiments of the present disclosure.

FIG. 12 illustrates the dC/dV response of a BPE device made from a single crystal of methylammonium lead iodide with symmetric gold contacts of 100 nm thickness. The metal used can be any non-reactive metal of any thickness, the crystal can be any of those compositions included here and can range from 100 nm to several millimeters in thickness. The initial scan shows the response of a typical resistor with the current equal to approximately zero (within the error of the instrument) when the voltage is 0. After poling the device, we get a non-zero current when V=0, both in the dark and under illumination. This demonstrates that poling has aligned the ferroelectric domains substantially and normal to the electrodes allowing for charge separation and collection.

Methods:

Crystal Growth, Characterization, and Preparation: Single crystals were prepared using an acid initiated solution growth method. Briefly, iodide salt solutions at 0.8 M in 4 ml fresh γ-butyrolactone were prepared by dissolving the salts at 55° C. with vigorous stirring for at least 30 minutes. The solution was filtered with a 0.45 μm syringe filter and placed in an oil bath at 95° C. in a closed crystallization dish. After the initial seed growth, an appropriate seed crystal (~0.5 mm) was placed in a similarly prepared solution and allowed to grow for 10-12 hours. The process was repeated multiple times until the crystal was of an appropriate size for the characterization technique. For the poling and EFM measurements double-sided, conductive copper tape was used to form electrical connection between the crystal and a conducting substrate. For the Rayleigh analysis and PFM100 nm thick gold electrodes were thermally evaporated on opposite facets of the crystal; electrical connection was made by adhering the bottom facet to a metalized substrate using silver paste and using a micro-probe to contact the top electrode.

TABLE 3

Single Crystal X-Ray Diffraction Indexing Results

| Compound | $CH_3NH_3PbI_3$ | |
|---|---|---|
| Growth temperature | | |
| Measurement temperature | 296K | |
| Space group | I4/m c m | I4 cm |
| Unit cell dimensions | a = 8.9018 ± 0.0003 Å | a = 8.9018 ± 0.0003 Å |
| | c = 12.6237 ± 0.0005 Å | c = 12.6237 ± 0.0005 Å |
| | α = β = γ = 90° | α = β = γ = 90° |
| Volume | 1000.33 Å$^3$ | 1000.33 Å$^3$ |
| Z | 4 | 4 |
| Reflections collected | 19866 | 19866 |
| Unique reflections | 256 | 484 |
| Inconsistent equivalents | 18 | 32 |
| R(int) | 0.1083 | 0.1072 |
| R (sigma) | 0.0780 | 0.1320 |
| Goodness-of-fit | 1.110 | 1.203 |
| Final R indices | 0.0773 | 0.1316 |
| Twin model | N/A | [1 0 0 0 1 0 0 0 -1] |
| Extinction coefficient | 0.003594 | 0.007768 |
| Wavelength | 0.71073 Å | 0.71073 Å |
| Weight scheme for the refinement | Weight = 1/[sigma$^2$ (Fo$^2$) + ( 0.0681 * P )$^2$ + 82.13 * P ] where P = ( Max ( Fo$^2$, 0 ) + 2 * Fc$^2$ )/3 | Weight = 1/[sigma$^2$ (Fo$^2$) + ( 0.0681 * P )$^2$ + 82.13 * P ] where P = ( Max ( Fo$^2$, 0 ) + 2 * Fc$^2$ )/3 |

Piezoresponse Force Microscopy: A 2 N/m platinum-coated tip (SCM-PIT-V2 Bruker) was used on a Bruker atomic force microscope system (Billerica, Mass.). During PFM measurements, an ac signal ranging from 20 mV up to 10 V was applied at 750 kHz. This frequency was chosen to avoid resonance. The response was measured statically on a well-defined gold top electrode. The response did not change over multiple sweeps taken over multiple days. Further static measurements were taken on the bare surface of the material, which showed a similar PFM response. All PFM and electrical measurements were taken with no illumination to reduce contributions from photo-generated carriers. For large signal measurements the domain reorientation by poling was duplicated in an external LCR measurement system.

Electrical Force Microscopy: The single crystals were mounted on an AFM sample holder via a conducting double-sided copper tape. The top surface of the crystal exposed to a high-voltage (i.e. poled) to facilitate ferroelectric domain formation (described in detail elsewhere). The EFM measurements were performed under ambient conditions using single pass mode on a Park AFM equipped with an XE-70 controller and an external lock-in amplifier (SR830, Stanford Research Systems). The external lock-in amplifier was used for electrical AC bias of the tip, lock-in detection and feedback at 18 kHz of the EFM signal. Conductive Pt/Ir-coated AFM tips (Multi-75EG, Budget Sensors) were used for the measurements. Topography was measured at the first resonance frequency (~75 kHz) and EFM was collected with a 1.00 Vac bias at 18 kHz, well separated from the topography frequency. The scan rate was 0.1 Hz. Surface topography and EFM were mapped simultaneously, while varying the sample bias voltages (0 to +/-10 V).

Electrical Measurements: The dielectric temperature and frequency dependence and Rayleigh behavior were measured using a precision LCR meter (Hewlett Packard 4284A, Palo Alto, Calif.), The heating and cooling rates were controlled by a Peltier heater, monitored by a type-K thermocouple, which was read via a digital multimeter (Hewlett Packard 3478). Samples were allowed to equilibrate for a two minutes prior to taking a measurement. Rayleigh behavior was characterized at 1 MHz. No changes were observed in the Rayleigh response upon multiple cycles of applied AC electric fields indicating that the response was not induced or affected by the application of this electric field. The temperature of the global phase transition temperature occurs at the same temperature for increasing and decreasing temperature sweeps within the limit of the experimental step size. Further information on the Rayleigh analysis methodology for indicating residual ferroelectricity can be found in Ref.[13]. Polarization-electric field measurements were taken on a Precision Multiferroic materials analyzer (Radiant Technologies, Inc., Albuquerque, N.M.).

The Rayleigh coefficient (see FIGS. 5A and 5B) was calculated from the slope of the AC electric field dependence of the permittivity. The total dielectric response, including the dielectric loss, is a combination of semiconductor and ferroelectric contributions. If only space-charge mechanisms were present, the permittivity and loss tangent should increase with temperature. The fact that the permittivity decreases as the temperature increases is consistent with relaxor ferroelectricity. This is also consistent with the loss of dispersion in the permittivity data above approximately 57° C.

Relaxor ferroelectricity should also cause frequency dispersion in the permittivity below $T_{max}$. FIGS. 9A and 9B show the dielectric response and loss for a MAPbI$_3$ single crystal as a function of temperature and frequency. Above 57° C. the frequency dispersion in the dielectric response does decrease but does not disappear, likely due to contributions from leakage current.

Density Functional Theory Calculations: First principles calculations were performed using the projector augmented wave (PAW) method as implemented in the Vienna Ab Initio Simulation Package (VASP). Structures were relaxed using the standard parameters of the Materials Project. Density functional perturbation (DFPT) calculations using the Perdew, Becke and Ernzerhof (PBE) Generalized Gradient Approximation (GGA) for the exchange-correlation functional, a plane wave cutoff of 1000 eV, and a k-point density of approximately 2,000 per reciprocal atom were employed to calculate the piezoelectric tensor. The elastic tensor was computed in DFT with a plane wave cutoff of 700 eV, and a k-point density of 7,000 per reciprocal atom using explicit perturbations of the lattice corresponding to the 6 principle deformations and fit assuming a linear relationship. The reported piezoelectric tensor was then computed by the dot product of the piezoelectric stress tensor computed via DFT and the computed compliance tensor.

XPS: Photoemission spectroscopy measurements were performed on a Kratos NOVA spectrometer calibrated to the Fermi edge and core level positions of sputter-cleaned metal (Au, Ag, Cu, Mo) surfaces. X-ray photoemission spectra were taken using mono-chromated Al Kα radiation (1486.7 eV) at a resolution of 400 meV and fit using Pseudo-Voigt profiles. Spectral acquisition were performed without light bias and using low X-ray fluences at nominal 1.5 W anode power.

$d_{33}$ Berlincourt Measurements and Analysis: The theoretical estimate calculated in this work for $d_{33}$ of 2.9 pC/N significantly underestimates the piezoelectric response. Plane wave based DFT codes are effective at predicting properties of periodic coupled systems such as inorganic crystals, but poor at describing the localized waves of molecular systems. These calculations are likely under-representing the contribution of the methyl ammonium to the polarization, which should be significant at 2.3 Debye. The under-prediction of the piezoelectric response by DFT suggests that the methyl ammonium molecule is largely responsible for the measured piezoelectricity. But the presence of any piezoelectric response when no response could be measured prior to poling further validates the presence of enduring reorientable dipoles within the material. Similar electrical measurements were taken on large, high quality single crystals of MAPbBr$_3$. MAPbBr$_3$ showed no Rayleigh response, or PFM response, which is consistent with the reported cubic crystal structure.

EXAMPLES

Example 1

A composition comprising a perovskite crystal comprising a ferroelectric domain aligned substantially parallel to a reference axis.

Example 2

The composition of Example 1, wherein: the perovskite crystal comprises ABX$_3$, wherein: A is a first cation, B is a second cation, and X is an anion.

Example 3

The composition of Example 2, wherein A comprises an alkyl ammonium cation.

Example 4

The composition of Example 2, wherein B comprises a metal element.

Example 5

The composition of Example 4, wherein the metal element comprises lead.

Example 6

The composition of Example 2, wherein X comprises a halogen.

Example 7

The composition of Example 2, wherein the perovskite crystal comprises methylammonium lead iodide.

Example 8

The composition of Example 1, wherein the ferroelectric domain has a crystal structure comprising at least one of a tetragonal phase or an orthorhombic phase.

Example 9

The composition of Example 1, wherein the ferroelectric domain has a crystal structure that is not a cubic phase.

Example 10

The composition of Example 1, wherein the ferroelectric domain is characterized by a Rayleigh response having a positive slope.

Example 11

The composition of Example 2, wherein the perovskite crystal comprises MAPI.

Example 12

The composition of Example 1, wherein the ferroelectric domain is characterized by a $d_{33}$ measurement having a value greater than zero pC/N.

Example 13

The composition of Example 12, wherein the $d_{33}$ measurement is between 0.1 pC/N and 10,000 pC/N.

Example 14

The composition of Example 1, wherein the ferroelectric domain is characterized by a characteristic value measured by at least one of piezoresponse force microscopy, electric force microscopy, contact Kelvin probe force microscopy, scanning microwave impedance microscopy, or optical microscopy.

Example 15

A device comprising a layer comprising a perovskite crystal comprising a ferroelectric domain aligned substantially parallel to a reference axis, wherein: the perovskite crystal comprises $ABX_3$, wherein: A is a first cation, B is a second cation, and X is an anion.

Example 16

The device of Example 15, wherein A comprises an alkyl ammonium cation.

Example 17

The device of Example 15, wherein B comprises a metal element.

Example 18

The device of Example 17, wherein the metal element comprises lead.

Example 19

The device of Example 15, wherein X comprises a halogen.

Example 20

The device of Example 15, wherein the perovskite crystal comprises methylammonium lead iodide.

Example 21

The device of Example 15, wherein the ferroelectric domain has a crystal structure comprising at least one of a tetragonal phase or an orthorhombic phase.

Example 22

The device of Example 15, wherein the ferroelectric domain has a crystal structure that is not a cubic phase.

Example 23

The device of Example 15, wherein the ferroelectric domain is characterized by a Rayleigh response having a positive slope.

Example 24

The device of Example 15, wherein the ferroelectric domain is characterized by a $d_{33}$ measurement having a value greater than zero pC/N.

Example 25

The device of Example 24, wherein the $d_{33}$ measurement is between 0.1 pC/N and 10,000 pC/N.

Example 26

The device of Example 15, wherein the ferroelectric domain is characterized by a characteristic value measured by at least one of piezoresponse force microscopy, electric force microscopy, contact Kelvin probe force microscopy, scanning microwave impedance microscopy, or optical microscopy.

Example 27

The device of Example 15, wherein: the layer further comprises a first surface and a second surface, the second surface is substantially parallel to the first surface, the first surface and the second surface define a thickness of the layer, and the reference axis is substantially perpendicular to the first surface and the second surface.

Example 28

The device of Example 27, wherein the thickness is between 1 Å and 10 mm.

Example 29

The device of Example 27, wherein the ferroelectric domain has a length between 1 Å and 10 mm.

Example 30

The device of Example 27, further comprising: a first electrode comprising a first metal positioned against the first surface; and a second electrode comprising a second metal positioned against the second surface, wherein: the layer is positioned between the first electrode and the second electrode.

Example 31

The device of Example 30, wherein the first metal and the second metal are the same.

Example 32

The device of Example 31, wherein the first metal and the second metal comprise gold.

Example 33

A method comprising: applying a gradient to a perovskite crystal having a characteristic length, wherein: the applying creates at least one ferroelectric domain within the perovskite crystal, the ferroelectric domain has a crystal structure that is not in a cubic phase, and the ferroelectric domain is aligned substantially parallel with the characteristic length.

Example 34

The method of Example 33, wherein the applying comprises at least one of applying an electric field gradient or a temperature gradient across the characteristic length.

Example 35

The method of Example 34, wherein the applying the electric field gradient comprises applying a voltage between 1 mV and 100 V across the characteristic length.

Example 36

The method of Example 34, wherein the temperature gradient is between 50° C./micrometer and 200° C./micrometer across the characteristic length.

Example 37

The method of Example 33, wherein the characteristic length is between 1 Å and 10 mm.

Example 38

The method of Example 35, wherein the applying is performed at a temperature between 15° C. and 25° C.

Example 39

The method of Example 35, wherein the applying is performed for a period of time between 1 second and 100 seconds.

Example 40

The method of Example 33, wherein: the perovskite crystal comprises $ABX_3$, wherein: A is a first cation, B is a second cation, and X is an anion.

Example 41

The method of Example 40, wherein A comprises an alkyl ammonium cation.

Example 42

The method of Example 40, wherein B comprises a metal element.

Example 43

The method of Example 42, wherein the metal element comprises lead.

Example 44

The method of Example 40, wherein X comprises a halogen.

Example 45

The method of Example 40 wherein the perovskite crystal comprises methylammonium lead iodide.

Example 46

The method of Example 33, wherein the ferroelectric domain has a crystal structure comprising at least one of a tetragonal phase or an orthorhombic phase.

Example 47

The method of Example 33, wherein the ferroelectric domain has a crystal structure that is not a cubic phase.

Example 48

The method of Example 33, wherein the ferroelectric domain is characterized by a Rayleigh response having a positive slope.

Example 49

The method of Example 33, wherein the ferroelectric domain is characterized by a $d_{33}$ measurement having a value greater than zero pC/N.

Example 50

The method of Example 49, wherein the $d_{33}$ measurement is between 0.1 pC/N and 10,000 pC/N.

Example 51

The method of Example 33, wherein the ferroelectric domain is characterized by a characteristic value measured by at least one of piezoresponse force microscopy, electric force microscopy, contact Kelvin probe force microscopy, scanning microwave impedance microscopy, or optical microscopy.

The foregoing discussion and examples have been presented for purposes of illustration and description. The foregoing is not intended to limit the aspects, embodiments, or configurations to the form or forms disclosed herein. In the foregoing Detailed Description for example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicants in no way disclaim these technical aspects, and it is contemplated that the claimed invention may encompass one or more of the conventional technical aspects discussed herein. Thus, the following claims are hereby incorporated into this Detailed Description, with each claim standing on its own as a separate aspect, embodiment, or configuration.

What is claimed is:

1. A composition comprising:
a methylammonium lead iodide perovskite crystal comprising a ferroelectric domain aligned substantially parallel to a reference axis, wherein:
the ferroelectric domain has a crystal structure consisting essentially of at least one of a tetragonal phase or an orthorhombic phase,
the ferroelectric domain has a width between 2 μm and 40 μm,
the ferroelectric domain has a length between one angstrom and 10 mm, and
the ferroelectric domain has a $d_{33}$ value between 50 pC/N and 60 pC/N.

2. The composition of claim 1, wherein the ferroelectric domain is characterized by a Rayleigh response having a positive slope.

3. A device comprising
a layer comprising a methylammonium lead iodide perovskite crystal comprising a ferroelectric domain aligned substantially parallel to a reference axis, wherein:
the ferroelectric domain has a crystal structure consisting essentially of at least one of a tetragonal phase or an orthorhombic phase,
the ferroelectric domain has a width between 2 μm and 40 μm,
the ferroelectric domain has a length between one angstrom and 10 mm, and
the ferroelectric domain has a $d_{33}$ value between 50 pC/N and 60 pC/N.

4. The device of claim 3, wherein:
the layer further comprises a first surface and a second surface,
the second surface is substantially parallel to the first surface,
the first surface and the second surface define a thickness of the layer, and
the reference axis is substantially perpendicular to the first surface and the second surface.

5. The device of claim 4, wherein the thickness is between 1 Å and 10 mm.

6. The device of claim 4, further comprising:
a first electrode comprising a first metal positioned against the first surface; and
a second electrode comprising a second metal positioned against the second surface, wherein:
the layer is positioned between the first electrode and the second electrode.

7. The device of claim 6, wherein the first metal and the second metal are the same.

* * * * *